(12) United States Patent
Ruiz Altaba

(10) Patent No.: US 9,518,098 B2
(45) Date of Patent: Dec. 13, 2016

(54) USES OF NANOG INHIBITORS AND RELATED METHODS

(75) Inventor: Ariel Ruiz Altaba, Geneva (CH)

(73) Assignee: UNIVERSITE DE GENEVE, Geneva (CH)

( * ) Notice: Subject to any disclaimer, the term of this patent is extended or adjusted under 35 U.S.C. 154(b) by 25 days.

(21) Appl. No.: 14/128,882

(22) PCT Filed: Jun. 25, 2012

(86) PCT No.: PCT/IB2012/053196
§ 371 (c)(1),
(2), (4) Date: Dec. 23, 2013

(87) PCT Pub. No.: WO2012/176175
PCT Pub. Date: Dec. 27, 2012

(65) Prior Publication Data
US 2014/0147440 A1    May 29, 2014

Related U.S. Application Data

(60) Provisional application No. 61/500,809, filed on Jun. 24, 2011.

(51) Int. Cl.
| | | |
|---|---|---|
| *C07K 19/00* | (2006.01) | |
| *C07H 21/02* | (2006.01) | |
| *C07K 14/435* | (2006.01) | |
| *A61K 31/7105* | (2006.01) | |
| *A61K 31/166* | (2006.01) | |
| *A61K 31/175* | (2006.01) | |
| *A61K 31/495* | (2006.01) | |
| *A61K 31/7088* | (2006.01) | |
| *A61K 38/12* | (2006.01) | |
| *A61K 38/17* | (2006.01) | |
| *A61K 39/395* | (2006.01) | |

(52) U.S. Cl.
CPC .......... *C07K 14/435* (2013.01); *A61K 31/166* (2013.01); *A61K 31/175* (2013.01); *A61K 31/495* (2013.01); *A61K 31/7088* (2013.01); *A61K 31/7105* (2013.01); *A61K 38/12* (2013.01); *A61K 38/17* (2013.01); *A61K 39/39533* (2013.01)

(58) Field of Classification Search
None
See application file for complete search history.

(56) References Cited

FOREIGN PATENT DOCUMENTS

| WO | WO2009/061837 | * | 5/2009 |
|---|---|---|---|
| WO | WO 2009/067563 | | 5/2009 |
| WO | WO 2010/100899 | | 9/2010 |
| WO | WO2010/135662 | * | 11/2010 |
| WO | WO2012/078586 | * | 6/2012 |

OTHER PUBLICATIONS

Wheeler (Salud p'ublica de M'exico, 1997, vol. 39, pp. 283-287).*
Zaehres et al (Stem Cells, 2005, vol. 23, pp. 299-305).*
Jauch et al (Journal of Molecular Biology, 2008, vol. 376, pp. 758-770).*
Database WPI, Accession No. 20120-L58612, 2010, Thomson Scientific, XP-002685191, pp. 1-3.
Katoh, M. "Network of WNT and Other Regulatory Signaling Cascades in Pluripotent Stem Cells and Cancer Stem Cells", *Current Pharmaceutical Biotechnology*, Feb. 1, 2011, pp. 160-170, vol. 12, No. 2.
Clement, V. et al. "Hedgehog-GLI1 Signaling Regulates Human Glioma Growth, Cancer Stem Cell Self-Renewal, and Tumorigenicity" *Current Biology*, Jan. 23, 2007, pp. 165-172, vol. 17.
Palma, V. et al. "Hedgehog-GLI signaling regulates the behavior of cells with stem cell properties in the developing neocortex" *Development*, 2003, pp. 337-345, vol. 131, No. 2.
Stecca, B. et al. "A GLI1-p53 inhibitory loop controls neural stem cell and tumour cell numbers" *The EMBO Journal*, 2009, pp. 663-676, vol. 28, No. 6.
Ben-Porath, I. et al. "An embryonic stem cell-like gene expression signature in poorly differentiated aggressive human tumors" *Nat Genet.*, May 2008, pp. 499-507, vol. 40, No. 5 and supplementary material (pp. 10-20).
Booth, H. et al. "Eleven daughters of NANOG" *Genomics*, 2004, pp. 229-238, vol. 84.
Chang, D. F. et al. "Molecular Characterization of the Human NANOG Protein" *Stem Cells*, 2009, pp. 812-821, vol. 27.
Zbinden, M. et al. "NANOG regulates glioma stem cells and is essential in vivo acting in a cross-functional network with GLI1 and p53" *The EMBO Journal*, 2010, pp. 2659-2674, vol. 29, No. 15.
Written Opinion in International Application No. PCT/IB2012/053196, Oct. 24, 2012, pp. 1-8.
Banerjee-Basu, S., et al., "Molecular evolution of the homeodomain family of transcription factors," *Nucleic Acids Research*, 2001, vol. 29, No. 15, pp. 3258-3269.

* cited by examiner

*Primary Examiner* — Karen Canella
(74) *Attorney, Agent, or Firm* — Saliwanchik, Lloyd & Eisenschenk

(57) ABSTRACT

The present invention relates to substances and compositions thereof useful in the control of cancer stem cell persistence and concomitant tumor recurrence and/or control of tumor growth. In particular, the invention relates to substances and compositions useful in the treatment of cancers and/or tumors linked to cancer stem cells, preferably brain cancers and/or tumors, in a subject.

17 Claims, 4 Drawing Sheets

SEQUENCE LISTING

<160> NUMBER OF SEQ ID NOS: 44

<210> SEQ ID NO 1
<211> LENGTH: 305
<212> TYPE: PRT
<213> ORGANISM: Homo sapiens

<400> SEQUENCE: 1

Met Ser Val Asp Pro Ala Cys Pro Gln Ser Leu Pro Cys Phe Glu Ala
1               5                   10                  15

Ser Asp Cys Lys Glu Ser Ser Pro Met Pro Val Ile Cys Gly Pro Glu
            20                  25                  30

Glu Asn Tyr Pro Ser Leu Gln Met Ser Ser Ala Glu Met Pro His Thr
            35                  40                  45

Glu Thr Val Ser Pro Leu Pro Ser Ser Met Asp Leu Leu Ile Gln Asp
        50                  55                  60

Ser Pro Asp Ser Ser Thr Ser Pro Lys Gly Lys Gln Pro Thr Ser Ala
65                  70                  75                  80

Glu Lys Ser Val Ala Lys Lys Glu Asp Lys Val Pro Val Lys Lys Gln
                85                  90                  95

Lys Thr Arg Thr Val Phe Ser Ser Thr Gln Leu Cys Val Leu Asn Asp
            100                 105                 110

Arg Phe Gln Arg Gln Lys Tyr Leu Ser Leu Gln Met Gln Glu Leu
            115                 120                 125

Ser Asn Ile Leu Asn Leu Ser Tyr Lys Gln Val Lys Thr Trp Phe Gln
            130                 135                 140

Asn Gln Arg Met Lys Ser Lys Arg Trp Gln Lys Asn Asn Trp Pro Lys
145                 150                 155                 160

Asn Ser Asn Gly Val Thr Gln Lys Ala Ser Ala Pro Thr Tyr Pro Ser
                165                 170                 175

Leu Tyr Ser Ser Tyr His Gln Gly Cys Leu Val Asn Pro Thr Gly Asn
            180                 185                 190

Leu Pro Met Trp Ser Asn Gln Thr Trp Asn Asn Ser Thr Trp Ser Asn
            195                 200                 205

Gln Thr Gln Asn Ile Gln Ser Trp Ser Asn His Ser Trp Asn Thr Gln
            210                 215                 220

Thr Trp Cys Thr Gln Ser Trp Asn Asn Gln Ala Trp Asn Ser Pro Phe
225                 230                 235                 240

Tyr Asn Cys Gly Glu Glu Ser Leu Gln Ser Cys Met Gln Phe Gln Pro
                245                 250                 255

Asn Ser Pro Ala Ser Asp Leu Glu Ala Ala Leu Glu Ala Ala Gly Glu
            260                 265                 270

Gly Leu Asn Val Ile Gln Gln Thr Thr Arg Tyr Phe Ser Thr Pro Gln
            275                 280                 285

Thr Met Asp Leu Phe Leu Asn Tyr Ser Met Asn Met Gln Pro Glu Asp
            290                 295                 300

Val
305

<210> SEQ ID NO 2
<211> LENGTH: 305
<212> TYPE: PRT
<213> ORGANISM: Homo sapiens

<400> SEQUENCE: 2

Met Ser Val Asp Pro Ala Cys Pro Gln Ser Leu Pro Cys Phe Glu Ala
1               5                   10                  15

Ser Asp Cys Lys Glu Ser Ser Pro Met Pro Val Ile Cys Gly Pro Glu
            20                  25                  30

Glu Asn Tyr Pro Ser Leu Gln Met Ser Ser Ala Glu Met Pro His Thr
            35                  40                  45

Glu Thr Val Ser Pro Leu Pro Ser Ser Met Asp Leu Leu Ile Gln Asp
        50                  55                  60

Ser Pro Asp Ser Ser Thr Ser Pro Lys Gly Lys Gln Pro Thr Ser Ala
65                  70                  75                  80

Glu Asn Ser Val Ala Lys Lys Glu Asp Lys Val Pro Val Lys Lys Gln

```
                    85                  90                  95
Lys Thr Arg Thr Val Phe Ser Ser Thr Gln Leu Cys Val Leu Asn Asp
                100                 105                 110

Arg Phe Gln Arg Gln Lys Tyr Leu Ser Leu Gln Gln Met Gln Glu Leu
            115                 120                 125

Ser Asn Ile Leu Asn Leu Ser Tyr Lys Gln Val Lys Thr Trp Phe Gln
        130                 135                 140

Asn Gln Arg Met Lys Ser Lys Arg Trp Gln Lys Asn Asn Trp Pro Lys
145                 150                 155                 160

Asn Ser Asn Gly Val Thr Gln Lys Ala Ser Ala Pro Thr Tyr Pro Ser
                165                 170                 175

Leu Tyr Ser Ser Tyr His Gln Gly Cys Leu Val Asn Pro Thr Gly Asn
            180                 185                 190

Leu Pro Met Trp Ser Asn Gln Thr Trp Asn Asn Ser Thr Trp Ser Asn
        195                 200                 205

Gln Thr Gln Asn Ile Gln Ser Trp Ser Asn His Ser Trp Asn Thr Gln
        210                 215                 220

Thr Trp Cys Thr Gln Ser Trp Asn Asn Gln Ala Trp Asn Ser Pro Phe
225                 230                 235                 240

Tyr Asn Cys Gly Glu Glu Ser Leu Gln Ser Cys Met Gln Phe Gln Pro
                245                 250                 255

Asn Ser Pro Ala Ser Asp Leu Glu Ala Ala Leu Glu Ala Ala Gly Glu
            260                 265                 270

Gly Leu Asn Val Ile Gln Gln Thr Thr Arg Tyr Phe Ser Thr Pro Gln
        275                 280                 285

Thr Met Asp Leu Phe Leu Asn Tyr Ser Met Asn Met Gln Pro Glu Asp
        290                 295                 300

Val
305

<210> SEQ ID NO 3
<211> LENGTH: 289
<212> TYPE: PRT
<213> ORGANISM: Homo sapiens

<400> SEQUENCE: 3

Met Ser Val Asp Pro Ala Cys Pro Gln Ser Leu Pro Cys Phe Glu Ala
1               5                   10                  15

Ser Asp Cys Lys Glu Ser Ser Pro Met Pro Val Ile Cys Gly Pro Glu
            20                  25                  30

Glu Asn Tyr Pro Ser Leu Gln Met Ser Ser Ala Glu Met Pro His Thr
        35                  40                  45

Glu Thr Val Ser Pro Leu Pro Ser Ser Met Asp Leu Leu Ile Gln Asp
    50                  55                  60

Ser Pro Asp Ser Ser Thr Ser Pro Lys Gly Lys Gln Pro Thr Ser Ala
65                  70                  75                  80

Glu Lys Ser Val Ala Lys Lys Glu Asp Lys Val Pro Val Lys Lys Gln
                85                  90                  95

Lys Thr Arg Thr Val Phe Ser Ser Thr Gln Leu Cys Val Leu Asn Asp
                100                 105                 110

Arg Phe Gln Arg Gln Lys Tyr Leu Ser Leu Gln Gln Met Gln Glu Leu
            115                 120                 125

Ser Asn Ile Leu Asn Leu Ser Tyr Lys Gln Val Lys Thr Trp Phe Gln
        130                 135                 140
```

```
Asn Gln Arg Met Lys Ser Lys Arg Trp Gln Lys Asn Asn Trp Pro Lys
145                 150                 155                 160

Asn Ser Asn Gly Val Thr Gln Gly Cys Leu Val Asn Pro Thr Gly Asn
                165                 170                 175

Leu Pro Met Trp Ser Asn Gln Thr Trp Asn Asn Ser Thr Trp Ser Asn
                180                 185                 190

Gln Thr Gln Asn Ile Gln Ser Trp Ser Asn His Ser Trp Asn Thr Gln
                195                 200                 205

Thr Trp Cys Thr Gln Ser Trp Asn Asn Gln Ala Trp Asn Ser Pro Phe
        210                 215                 220

Tyr Asn Cys Gly Glu Glu Ser Leu Gln Ser Cys Met Gln Phe Gln Pro
225                 230                 235                 240

Asn Ser Pro Ala Ser Asp Leu Glu Ala Ala Leu Glu Ala Ala Gly Glu
                245                 250                 255

Gly Leu Asn Val Ile Gln Gln Thr Thr Arg Tyr Phe Ser Thr Pro Gln
                260                 265                 270

Thr Met Asp Leu Phe Leu Asn Tyr Ser Met Asn Met Gln Pro Glu Asp
            275                 280                 285

Val

<210> SEQ ID NO 4
<211> LENGTH: 305
<212> TYPE: PRT
<213> ORGANISM: Homo sapiens

<400> SEQUENCE: 4

Met Ser Val Asp Pro Ala Cys Pro Gln Ser Leu Pro Cys Phe Glu Ala
1               5                   10                  15

Ser Asp Cys Lys Glu Ser Ser Pro Met Pro Val Ile Cys Gly Pro Glu
                20                  25                  30

Glu Asn Tyr Pro Ser Leu Gln Met Ser Ser Ala Glu Met Pro His Thr
            35                  40                  45

Glu Thr Val Ser Pro Leu Pro Ser Ser Met Asp Leu Leu Ile Gln Asp
    50                  55                  60

Ser Pro Asp Ser Ser Thr Ser Pro Lys Gly Lys Gln Pro Thr Ser Ala
65                  70                  75                  80

Glu Asn Ser Val Ala Lys Lys Glu Asp Lys Val Pro Val Lys Lys Gln
                85                  90                  95

Lys Thr Arg Thr Val Phe Ser Ser Thr Gln Leu Cys Val Leu Asn Asp
                100                 105                 110

Arg Phe Gln Arg Gln Lys Tyr Leu Ser Leu Gln Gln Met Gln Glu Leu
            115                 120                 125

Ser Asn Ile Leu Asn Leu Ser Tyr Lys Gln Val Lys Thr Trp Phe Gln
130                 135                 140

Asn Gln Arg Met Lys Ser Lys Arg Trp Gln Lys Asn Asn Trp Pro Lys
145                 150                 155                 160

Asn Ser Asn Gly Val Thr Gln Lys Ala Ser Ala Pro Thr Tyr Pro Ser
                165                 170                 175

Leu Tyr Ser Ser Tyr His Gln Gly Cys Leu Val Asn Pro Thr Gly Asn
                180                 185                 190

Leu Pro Met Trp Ser Asn Gln Thr Trp Asn Asn Ser Thr Trp Ser Asn
                195                 200                 205

Gln Thr Gln Asn Ile Gln Ser Trp Ser Asn His Ser Trp Asn Thr Gln
            210                 215                 220
```

```
Thr Trp Cys Thr Gln Ser Trp Asn Asn Gln Ala Trp Asn Ser Pro Phe
225                 230                 235                 240

Tyr Asn Cys Gly Glu Glu Ser Leu Gln Ser Cys Met His Phe Gln Pro
            245                 250                 255

Asn Ser Pro Ala Ser Asp Leu Glu Ala Ala Leu Glu Ala Ala Gly Glu
        260                 265                 270

Gly Leu Asn Val Ile Gln Gln Thr Thr Arg Tyr Phe Ser Thr Pro Gln
    275                 280                 285

Thr Met Asp Leu Phe Leu Asn Tyr Ser Met Asn Met Gln Pro Glu Asp
    290                 295                 300

Val
305

<210> SEQ ID NO 5
<211> LENGTH: 60
<212> TYPE: PRT
<213> ORGANISM: Homo sapiens

<400> SEQUENCE: 5

Lys Gln Lys Thr Arg Thr Val Phe Ser Ser Thr Gln Leu Cys Val Leu
1               5                   10                  15

Asn Asp Arg Phe Gln Arg Gln Lys Tyr Leu Ser Leu Gln Gln Met Gln
            20                  25                  30

Glu Leu Ser Asn Ile Leu Asn Leu Ser Tyr Lys Gln Val Lys Thr Trp
        35                  40                  45

Phe Gln Asn Gln Arg Met Lys Ser Lys Arg Trp Gln
    50                  55                  60

<210> SEQ ID NO 6
<211> LENGTH: 305
<212> TYPE: PRT
<213> ORGANISM: Mus musculus

<400> SEQUENCE: 6

Met Ser Val Gly Leu Pro Gly Pro His Ser Leu Pro Ser Ser Glu Glu
1               5                   10                  15

Ala Ser Asn Ser Gly Asn Ala Ser Met Pro Ala Val Phe His Pro Pro
            20                  25                  30

Glu Asn Tyr Ser Cys Leu Gln Gly Ser Ala Thr Glu Met Leu Cys Thr
        35                  40                  45

Glu Ala Ala Ser Pro Arg Pro Ser Ser Glu Asp Leu Pro Leu Gln Gly
    50                  55                  60

Ser Pro Asp Ser Ser Thr Ser Pro Lys Gln Lys Leu Ser Ser Pro Glu
65                  70                  75                  80

Ala Asp Lys Gly Pro Glu Glu Glu Asn Lys Val Leu Ala Arg Lys
            85                  90                  95

Gln Lys Met Arg Thr Val Phe Ser Gln Ala Gln Leu Cys Ala Leu Lys
        100                 105                 110

Asp Arg Phe Gln Lys Gln Lys Tyr Leu Ser Leu Gln Gln Met Gln Glu
    115                 120                 125

Leu Ser Ser Ile Leu Asn Leu Ser Tyr Lys Gln Val Lys Thr Trp Phe
130                 135                 140

Gln Asn Gln Arg Met Lys Cys Lys Arg Trp Gln Lys Asn Gln Trp Leu
145                 150                 155                 160

Lys Thr Ser Asn Gly Leu Ile Gln Lys Gly Ser Ala Pro Val Glu Tyr
            165                 170                 175
```

```
Pro Ser Ile His Cys Ser Tyr Pro Gln Gly Tyr Leu Val Asn Ala Ser
            180                 185                 190

Gly Ser Leu Ser Met Trp Gly Ser Gln Thr Trp Thr Asn Pro Thr Trp
        195                 200                 205

Ser Ser Gln Thr Trp Thr Asn Pro Thr Trp Asn Asn Gln Thr Trp Thr
210                 215                 220

Asn Pro Thr Trp Ser Ser Gln Ala Trp Thr Ala Gln Ser Trp Asn Gly
225                 230                 235                 240

Gln Pro Trp Asn Ala Ala Pro Leu His Asn Phe Gly Glu Asp Phe Leu
                245                 250                 255

Gln Pro Tyr Val Gln Leu Gln Gln Asn Phe Ser Ala Ser Asp Leu Glu
            260                 265                 270

Val Asn Leu Glu Ala Thr Arg Glu Ser His Ala His Phe Ser Thr Pro
        275                 280                 285

Gln Ala Leu Glu Leu Phe Leu Asn Tyr Ser Val Thr Pro Pro Gly Glu
    290                 295                 300

Ile
305

<210> SEQ ID NO 7
<211> LENGTH: 300
<212> TYPE: PRT
<213> ORGANISM: Bos taurus

<400> SEQUENCE: 7

Met Ser Val Gly Pro Ala Cys Pro Gln Ser Leu Leu Gly Pro Glu Ala
1               5                   10                  15

Ser Asn Ser Arg Glu Ser Ser Pro Met Pro Glu Glu Ser Tyr Val Ser
            20                  25                  30

Leu Gln Thr Ser Ser Ala Asp Thr Leu Asp Thr Asp Val Ser Pro
        35                  40                  45

Leu Pro Ser Ser Met Asp Leu Leu Ile Gln Asp Ser Pro Asp Ser Ser
    50                  55                  60

Thr Ser Pro Arg Val Lys Pro Leu Ser Pro Ser Val Glu Glu Ser Thr
65                  70                  75                  80

Glu Lys Glu Glu Thr Val Pro Val Lys Lys Gln Lys Ile Arg Thr Val
                85                  90                  95

Phe Ser Gln Thr Gln Leu Cys Val Leu Asn Asp Arg Phe Gln Arg Gln
            100                 105                 110

Lys Tyr Leu Ser Leu Gln Gln Met Gln Glu Leu Ser Asn Ile Leu Asn
        115                 120                 125

Leu Ser Tyr Lys Gln Val Lys Thr Trp Phe Gln Asn Gln Arg Met Lys
    130                 135                 140

Cys Lys Lys Trp Gln Lys Asn Asn Trp Pro Arg Asn Ser Asn Gly Met
145                 150                 155                 160

Pro Gln Gly Pro Ala Met Ala Glu Tyr Pro Gly Phe Tyr Ser Tyr His
                165                 170                 175

Gln Gly Cys Leu Val Asn Ser Pro Gly Asn Leu Pro Met Trp Gly Asn
            180                 185                 190

Gln Thr Trp Asn Asn Pro Thr Trp Ser Asn Gln Ser Trp Asn Ser Gln
        195                 200                 205

Ser Trp Ser Asn His Ser Trp Asn Ser Gln Ala Trp Cys Pro Gln Ala
    210                 215                 220

Trp Asn Asn Gln Pro Trp Asn Asn Gln Phe Asn Asn Tyr Met Glu Glu
225                 230                 235                 240
```

```
Phe Leu Gln Pro Gly Ile Gln Leu Gln Gln Asn Ser Pro Val Cys Asp
                245                 250                 255
Leu Glu Ala Thr Leu Gly Thr Ala Gly Glu Asn Tyr Asn Val Ile Gln
            260                 265                 270
Gln Thr Val Lys Tyr Phe Asn Ser Gln Gln Ile Thr Asp Leu Phe
        275                 280                 285
Pro Asn Tyr Pro Leu Asn Ile Gln Pro Glu Asp Leu
    290                 295                 300

<210> SEQ ID NO 8
<211> LENGTH: 311
<212> TYPE: PRT
<213> ORGANISM: Rattus norvegicus

<400> SEQUENCE: 8

Met Ser Val Asp Leu Ser Gly Pro His Ser Leu Pro Ser Cys Glu Glu
1               5                   10                  15
Ala Ser Asn Ser Gly Asp Ser Ser Pro Met Pro Ala Val His Leu Pro
            20                  25                  30
Glu Glu Asn Tyr Ser Cys Leu Gln Val Ser Ala Thr Glu Met Leu Cys
        35                  40                  45
Thr Glu Thr Ala Ser Pro Pro Pro Ser Ser Gly Asp Leu Pro Leu Gln
    50                  55                  60
Asp Ser Pro Asp Ser Ser Ser Asn Pro Lys Leu Lys Leu Ser Gly Pro
65                  70                  75                  80
Arg Leu Thr Arg Ala Leu Arg Arg Lys Lys Arg Thr Arg Ser Ser Pro
                85                  90                  95
Arg Lys Gln Lys Met Arg Thr Val Phe Ser Gln Ala Gln Leu Cys Ala
            100                 105                 110
Leu Lys Asp Arg Phe Gln Arg Gln Arg Tyr Leu Ser Leu Gln Gln Met
        115                 120                 125
Gln Asp Leu Ser Thr Ile Leu Ser Leu Ser Tyr Lys Gln Val Lys Thr
    130                 135                 140
Trp Phe Gln Asn Gln Arg Met Lys Cys Lys Arg Trp Gln Lys Asn Gln
145                 150                 155                 160
Trp Leu Lys Thr Ser Asn Gly Leu Thr Gln Gly Ser Ala Pro Val Glu
                165                 170                 175
Tyr Pro Ser Ile His Cys Ser Tyr Ser Gln Gly Tyr Leu Met Asn Ala
            180                 185                 190
Ser Gly Asn Leu Pro Val Trp Gly Ser Gln Thr Trp Thr Asn Pro Thr
        195                 200                 205
Trp Asn Asn Gln Thr Trp Thr Asn Pro Thr Trp Ser Asn Gln Thr Trp
    210                 215                 220
Thr Asn Pro Thr Trp Ser Asn Gln Ala Trp Ser Thr Gln Ser Trp Cys
225                 230                 235                 240
Thr Gln Ala Cys Asn Ser Gln Thr Trp Asn Ala Ala Pro Leu His Asn
                245                 250                 255
Phe Gly Glu Asp Ser Leu Gln Pro Tyr Val Pro Leu Gln Gln Asn Phe
            260                 265                 270
Ser Ala Ser Asp Leu Glu Ala Asn Leu Glu Ala Thr Arg Glu Ser Gln
        275                 280                 285
Ala His Phe Ser Thr Pro Gln Ala Leu Glu Leu Phe Leu Asn Tyr Ser
    290                 295                 300
Val Asn Ser Pro Gly Glu Ile
```

<210> SEQ ID NO 9
<211> LENGTH: 918
<212> TYPE: DNA
<213> ORGANISM: Homo sapiens

<400> SEQUENCE: 9

```
atgagtgtgg atccagcttg tccccaaagc ttgccttgct ttgaagcatc cgactgtaaa      60
gaatcttcac ctatgcctgt gatttgtggg cctgaagaaa actatccatc cttgcaaatg     120
tcttctgctg agatgcctca cacggagact gtctctcctc ttccttcctc catggatctg     180
cttattcagg acagccctga ttcttccacc agtcccaaag caaacaacc cacttctgca      240
gagaagagtg tcgcaaaaaa ggaagacaag gtcccggtca agaaacagaa gaccagaact     300
gtgttctctt ccacccagct gtgtgtactc aatgatagat tcagagaca gaaatacctc      360
agcctccagc agatgcaaga actctccaac atcctgaacc tcagctacaa acaggtgaag     420
acctggttcc agaaccagag aatgaaatct aagaggtggc agaaaaacaa ctggccgaag     480
aatagcaatg gtgtgacgca gaaggcctca gcacctacct accccagcct tactcttcc      540
taccaccagg gatgcctggt gaacccgact gggaacttc aatgtggag caaccagacc       600
tggaacaatt caacctggag caaccagacc cagaacatcc agtcctggag caaccactcc     660
tggaacactc agacctggtg cacccaatcc tggaacaatc aggcctggaa cagtcccttc     720
tataactgtg gagaggaatc tctgcagtcc tgcatgcagt tccagccaaa ttctcctgcc     780
agtgacttgg aggctgcctt ggaagctgct ggggaaggcc ttaatgtaat acagcagacc     840
actaggtatt ttagtactcc acaaaccatg gatttattcc taaactactc catgaacatg     900
caacctgaag acgtgtga                                                    918
```

<210> SEQ ID NO 10
<211> LENGTH: 918
<212> TYPE: DNA
<213> ORGANISM: Homo sapiens

<400> SEQUENCE: 10

```
atgagtgtgg atccagcttg tccccaaagc ttgccttgct ttgaagaatc cgactgtaaa      60
gaatcttcac ctatgcctgt gatttgtggg cctgaagaaa actatccatc cttgcaaatg     120
tcttctgctg agatgcctca cacagagact gtctctcctc ttccttcctc catggatctg     180
cttattcagg acagccctga ttcttccacc agtcccaaag caaacaacc cacttctgca      240
gagaatagtg tcgcaaaaaa ggaagacaag gtcccggtca agaaacagaa gaccagaact     300
gtgttctctt ccacccagct gtgtgtactc aatgatagat tcagagaca gaaatacctc      360
agcctccagc agatgcaaga actctccaac atcctgaacc tcagctacaa acaggtgaag     420
acctggttcc agaaccagag aatgaaatct aagaggtggc agaaaaacaa ctggccgaag     480
aatagcaatg gtgtgacgca gaaggcctca gcacctacct accccagcct ctactcttcc     540
taccaccagg gatgcctggt gaacccgact gggaacttc aatgtggag caaccagacc       600
tggaacaatt caacctggag caaccagacc cagaacatcc agtcctggag caaccactcc     660
tggaacactc agacctggtg cacccaatcc tggaacaatc aggcctggaa cagtcccttc     720
tataactgtg gagaggaatc tctgcagtcc tgcatgcact tccagccaaa ttctcctgcc     780
agtgacttgg aggctgcctt ggaagctgct ggggaaggcc ttaatgtaat acagcagacc     840
actaggtatt ttagtactcc acaaaccatg gatttattcc taaactactc catgaacatg     900
```

```
caacctgaag acgtgtga                                                    918
```

<210> SEQ ID NO 11
<211> LENGTH: 21
<212> TYPE: DNA
<213> ORGANISM: Artificial Sequence
<220> FEATURE:
<223> OTHER INFORMATION: shNANOG1

<400> SEQUENCE: 11

```
gggttaagct gtaacatact t                                                 21
```

<210> SEQ ID NO 12
<211> LENGTH: 21
<212> TYPE: DNA
<213> ORGANISM: Artificial Sequence
<220> FEATURE:
<223> OTHER INFORMATION: shNANOG2

<400> SEQUENCE: 12

```
cctggaacag tcccttctat a                                                 21
```

<210> SEQ ID NO 13
<211> LENGTH: 22
<212> TYPE: DNA
<213> ORGANISM: Artificial Sequence
<220> FEATURE:
<223> OTHER INFORMATION: shNANOGP8

<400> SEQUENCE: 13

```
aacaaagcac atcttgccag ga                                                22
```

<210> SEQ ID NO 14
<211> LENGTH: 24
<212> TYPE: DNA
<213> ORGANISM: Artificial Sequence
<220> FEATURE:
<223> OTHER INFORMATION: NANOG and NANOGP8 forward primer

<400> SEQUENCE: 14

```
aaattggtga tgaagatgta ttcg                                              24
```

<210> SEQ ID NO 15
<211> LENGTH: 20
<212> TYPE: DNA
<213> ORGANISM: Artificial Sequence
<220> FEATURE:
<223> OTHER INFORMATION: NANOG and NANOGP8 reverse primer

<400> SEQUENCE: 15

```
gcaaaacaga gccaaaaacg                                                   20
```

<210> SEQ ID NO 16
<211> LENGTH: 20
<212> TYPE: DNA
<213> ORGANISM: Artificial Sequence
<220> FEATURE:
<223> OTHER INFORMATION: NANOGP8 forward primer

<400> SEQUENCE: 16

```
gctgccttca agcatctgtt                                                   20
```

<210> SEQ ID NO 17
<211> LENGTH: 21
<212> TYPE: DNA

```
<213> ORGANISM: Artificial Sequence
<220> FEATURE:
<223> OTHER INFORMATION: NANOGP8 reverse primer

<400> SEQUENCE: 17
ttgtttgcct ttgggactgg t                                         21

<210> SEQ ID NO 18
<211> LENGTH: 20
<212> TYPE: DNA
<213> ORGANISM: Artificial Sequence
<220> FEATURE:
<223> OTHER INFORMATION: NANOG and NANOGP8 3'UTR forward primer

<400> SEQUENCE: 18
ggatggtctc gatctcctga                                           20

<210> SEQ ID NO 19
<211> LENGTH: 20
<212> TYPE: DNA
<213> ORGANISM: Artificial Sequence
<220> FEATURE:
<223> OTHER INFORMATION: NANOG and NANOGP8 3'UTR reverse primer

<400> SEQUENCE: 19
cccaatccca aacaatacga                                           20

<210> SEQ ID NO 20
<211> LENGTH: 23
<212> TYPE: DNA
<213> ORGANISM: Artificial Sequence
<220> FEATURE:
<223> OTHER INFORMATION: beta ACTIN forward primer

<400> SEQUENCE: 20
tggagaaaat ctggcaccac acc                                       23

<210> SEQ ID NO 21
<211> LENGTH: 23
<212> TYPE: DNA
<213> ORGANISM: Artificial Sequence
<220> FEATURE:
<223> OTHER INFORMATION: beta ACTIN reverse primer

<400> SEQUENCE: 21
gatgggcaca gtgtgggtga ccc                                       23

<210> SEQ ID NO 22
<211> LENGTH: 21
<212> TYPE: DNA
<213> ORGANISM: Artificial Sequence
<220> FEATURE:
<223> OTHER INFORMATION: TBP forward primer

<400> SEQUENCE: 22
tgcacaggag ccaagagtga a                                         21

<210> SEQ ID NO 23
<211> LENGTH: 20
<212> TYPE: DNA
<213> ORGANISM: Artificial Sequence
<220> FEATURE:
<223> OTHER INFORMATION: TBP reverse primer

<400> SEQUENCE: 23
cacatcacag ctccccacca                                           20
```

<210> SEQ ID NO 24
<211> LENGTH: 22
<212> TYPE: DNA
<213> ORGANISM: Artificial Sequence
<220> FEATURE:
<223> OTHER INFORMATION: PTCH1 forward primer

<400> SEQUENCE: 24
ggcagcggta gtagtggtgt tc                                            22

<210> SEQ ID NO 25
<211> LENGTH: 23
<212> TYPE: DNA
<213> ORGANISM: Artificial Sequence
<220> FEATURE:
<223> OTHER INFORMATION: PTCH1 reverse primer

<400> SEQUENCE: 25
tgtagcgggt attgtcgtgt gtg                                           23

<210> SEQ ID NO 26
<211> LENGTH: 20
<212> TYPE: DNA
<213> ORGANISM: Artificial Sequence
<220> FEATURE:
<223> OTHER INFORMATION: SMOH forward primer

<400> SEQUENCE: 26
gggaggctac ttcctcatcc                                               20

<210> SEQ ID NO 27
<211> LENGTH: 20
<212> TYPE: DNA
<213> ORGANISM: Artificial Sequence
<220> FEATURE:
<223> OTHER INFORMATION: SMOH reverse primer

<400> SEQUENCE: 27
ggcagctgaa ggtaatgagc                                               20

<210> SEQ ID NO 28
<211> LENGTH: 20
<212> TYPE: DNA
<213> ORGANISM: Artificial Sequence
<220> FEATURE:
<223> OTHER INFORMATION: TP53 forward primer

<400> SEQUENCE: 28
gtggaaggaa atttgcgtgt                                               20

<210> SEQ ID NO 29
<211> LENGTH: 20
<212> TYPE: DNA
<213> ORGANISM: Artificial Sequence
<220> FEATURE:
<223> OTHER INFORMATION: TP53 reverse primer

<400> SEQUENCE: 29
ccagtgtgat gatggtgagg                                               20

<210> SEQ ID NO 30
<211> LENGTH: 20
<212> TYPE: DNA
<213> ORGANISM: Artificial Sequence
<220> FEATURE:

```
<223> OTHER INFORMATION: SUFUH forward primer

<400> SEQUENCE: 30
ggctttgagt tgacctttcg                                              20

<210> SEQ ID NO 31
<211> LENGTH: 20
<212> TYPE: DNA
<213> ORGANISM: Artificial Sequence
<220> FEATURE:
<223> OTHER INFORMATION: SUFUH reverse primer

<400> SEQUENCE: 31
catctgtggg tcctctgtca                                              20

<210> SEQ ID NO 32
<211> LENGTH: 20
<212> TYPE: DNA
<213> ORGANISM: Artificial Sequence
<220> FEATURE:
<223> OTHER INFORMATION: 3'UTR forward primer for sequencing

<400> SEQUENCE: 32
gagacggggt ttcactgtgt                                              20

<210> SEQ ID NO 33
<211> LENGTH: 21
<212> TYPE: DNA
<213> ORGANISM: Artificial Sequence
<220> FEATURE:
<223> OTHER INFORMATION: 3'UTR reverse primer for sequencing

<400> SEQUENCE: 33
cactcggtga aatcagggta a                                            21

<210> SEQ ID NO 34
<211> LENGTH: 11
<212> TYPE: DNA
<213> ORGANISM: Artificial Sequence
<220> FEATURE:
<223> OTHER INFORMATION: consensus sequence
<220> FEATURE:
<221> NAME/KEY: misc_feature
<222> LOCATION: (10)..(10)
<223> OTHER INFORMATION: n is a, c, g, or t

<400> SEQUENCE: 34
srscsattan s                                                       11

<210> SEQ ID NO 35
<211> LENGTH: 45
<212> TYPE: PRT
<213> ORGANISM: Homo sapiens

<400> SEQUENCE: 35

Trp Ser Asn Gln Thr Trp Asn Asn Ser Thr Trp Ser Asn Gln Thr Gln
 1               5                  10                  15

Asn Ile Gln Ser Trp Ser Asn His Ser Trp Asn Thr Gln Thr Trp Cys
                20                  25                  30

Thr Gln Ser Trp Asn Asn Gln Ala Trp Asn Ser Pro Phe
            35                  40                  45

<210> SEQ ID NO 36
<211> LENGTH: 298
<212> TYPE: PRT
```

<213> ORGANISM: Homo sapiens

<400> SEQUENCE: 36

```
Met Glu Glu Gln Gln Pro Glu Pro Lys Ser Gln Arg Asp Ser Ala Leu
1               5                   10                  15
Gly Gly Ala Ala Ala Thr Pro Gly Gly Leu Ser Leu Ser Leu Ser
            20                  25                  30
Pro Gly Ala Ser Gly Ser Ser Gly Ser Gly Ser Asp Gly Asp Ser Val
        35                  40                  45
Pro Val Ser Pro Gln Pro Ala Pro Ser Pro Pro Ala Ala Pro Cys
    50                  55                  60
Leu Pro Pro Leu Ala His His Pro His Leu Pro His Pro Pro
65                  70                  75                  80
Pro Pro Pro Gln His Leu Ala Ala Pro Ala His Gln Pro Gln Pro Ala
                85                  90                  95
Ala Gln Leu His Arg Thr Thr Asn Phe Phe Ile Asp Asn Ile Leu Arg
            100                 105                 110
Pro Asp Phe Gly Cys Lys Lys Glu Gln Pro Pro Gln Leu Leu Val
        115                 120                 125
Ala Ala Ala Ala Arg Gly Gly Ala Gly Gly Gly Arg Val Glu Arg
    130                 135                 140
Asp Arg Gly Gln Thr Ala Ala Gly Arg Asp Pro Val His Pro Leu Gly
145                 150                 155                 160
Thr Arg Ala Pro Gly Ala Ala Ser Leu Leu Cys Ala Pro Asp Ala Asn
                165                 170                 175
Cys Gly Pro Pro Asp Gly Ser Gln Pro Ala Ala Ala Gly Ala Gly Ala
            180                 185                 190
Ser Lys Ala Gly Asn Pro Ala Ala Ala Ala Ala Ala Ala Ala
        195                 200                 205
Val Ala Ala Ala Ala Ala Ala Ala Lys Pro Ser Asp Thr Gly
    210                 215                 220
Gly Gly Gly Ser Gly Gly Gly Ala Gly Ser Pro Gly Ala Gln Gly Thr
225                 230                 235                 240
Lys Tyr Pro Glu His Gly Asn Pro Ala Ile Leu Leu Met Gly Ser Ala
                245                 250                 255
Asn Gly Gly Pro Val Val Lys Thr Asp Ser Gln Gln Pro Leu Val Trp
            260                 265                 270
Pro Ala Trp Val Tyr Cys Thr Arg Tyr Ser Asp Arg Pro Ser Ser Gly
        275                 280                 285
Pro Arg Thr Arg Lys Leu Lys Lys Lys
    290                 295
```

<210> SEQ ID NO 37
<211> LENGTH: 26
<212> TYPE: PRT
<213> ORGANISM: Homo sapiens

<400> SEQUENCE: 37

```
Val Pro Ser Ile Leu Ser Leu Ile Gln Thr Pro Lys Cys Leu His Thr
1               5                   10                  15
Tyr Phe Ser Met Thr Thr Met Gly Asn Thr
            20                  25
```

<210> SEQ ID NO 38
<211> LENGTH: 296
<212> TYPE: PRT

<213> ORGANISM: Drosophila melanogaster

<400> SEQUENCE: 38

Met Ala Leu Glu Asp Arg Cys Ser Pro Gln Ser Ala Pro Ser Pro Ile
1               5                   10                  15

Thr Leu Gln Met Gln His Leu His His Gln Gln Gln Gln Gln Gln Gln
            20                  25                  30

Gln Gln Gln Gln Met Gln His Leu His Gln Leu Gln Gln Leu Gln Gln
        35                  40                  45

Leu His Gln Gln Gln Leu Ala Ala Gly Val Phe His His Pro Ala Met
    50                  55                  60

Ala Phe Asp Ala Ala Ala Ala Ala Ala Ala Ala Ala Ala Ala Ala Ala
65                  70                  75                  80

Ala His Ala His Ala Ala Leu Gln Gln Arg Leu Ser Gly Ser Gly
                85                  90                  95

Ser Pro Ala Ser Cys Ser Thr Pro Ala Ser Ser Thr Pro Leu Thr Ile
            100                 105                 110

Lys Glu Glu Glu Ser Asp Ser Val Ile Gly Asp Met Ser Phe His Asn
        115                 120                 125

Gln Thr His Thr Thr Asn Glu Glu Glu Ala Glu Glu Asp Asp
    130                 135                 140

Ile Asp Val Asp Val Asp Asp Thr Ser Ala Gly Gly Arg Leu Pro Pro
145                 150                 155                 160

Pro Ala His Gln Gln Gln Ser Thr Ala Lys Pro Ser Leu Ala Phe Ser
                165                 170                 175

Ile Ser Asn Ile Leu Ser Asp Arg Phe Gly Asp Val Gln Lys Pro Gly
            180                 185                 190

Lys Ser Met Glu Asn Gln Ala Ser Ile Phe Arg Pro Phe Glu Ala Ser
        195                 200                 205

Arg Ser Gln Thr Ala Thr Pro Ser Ala Phe Thr Arg Val Asp Leu Leu
    210                 215                 220

Glu Phe Ser Arg Gln Gln Gln Ala Ala Ala Ala Ala Thr Ala Ala
225                 230                 235                 240

Met Met Leu Glu Arg Ala Asn Phe Leu Asn Cys Phe Asn Pro Ala Ala
                245                 250                 255

Tyr Pro Arg Ile His Glu Glu Ile Val Gln Ser Arg Leu Arg Arg Ser
            260                 265                 270

Ala Ala Asn Ala Val Ile Pro Pro Met Ser Ser Lys Met Ser Asp
    275                 280                 285

Ala Asn Pro Glu Lys Ser Ala Leu
    290                 295

<210> SEQ ID NO 39
<211> LENGTH: 25
<212> TYPE: PRT
<213> ORGANISM: Homo sapiens

<400> SEQUENCE: 39

Met Asp Ala Thr Trp Leu Asp Ser Leu Leu Thr Pro Val Arg Leu Pro
1               5                   10                  15

Ser Ile Gln Ala Ile Pro Cys Ala Pro
            20                  25

<210> SEQ ID NO 40
<211> LENGTH: 16
<212> TYPE: PRT

```
<213> ORGANISM: Drosophila melanogaster

<400> SEQUENCE: 40

Arg Gln Ile Lys Ile Trp Phe Gln Asn Arg Arg Met Lys Trp Lys Lys
1               5                   10                  15

<210> SEQ ID NO 41
<211> LENGTH: 9
<212> TYPE: PRT
<213> ORGANISM: Artificial Sequence
<220> FEATURE:
<223> OTHER INFORMATION: glioma targeting peptide

<400> SEQUENCE: 41

Cys Arg Thr Ile Gly Pro Ser Val Cys
1               5

<210> SEQ ID NO 42
<211> LENGTH: 8
<212> TYPE: PRT
<213> ORGANISM: Artificial Sequence
<220> FEATURE:
<223> OTHER INFORMATION: FLAG Tag

<400> SEQUENCE: 42

Asp Tyr Lys Asp Asp Asp Asp Lys
1               5

<210> SEQ ID NO 43
<211> LENGTH: 9
<212> TYPE: PRT
<213> ORGANISM: Artificial Sequence
<220> FEATURE:
<223> OTHER INFORMATION: HA Tag

<400> SEQUENCE: 43

Tyr Pro Tyr Asp Val Pro Asp Tyr Ala
1               5

<210> SEQ ID NO 44
<211> LENGTH: 4
<212> TYPE: PRT
<213> ORGANISM: Artificial Sequence
<220> FEATURE:
<223> OTHER INFORMATION: WRPW motif of the hairy-related protein

<400> SEQUENCE: 44

Trp Arg Pro Trp
1
```

USES OF NANOG INHIBITORS AND RELATED METHODS

CROSS-REFERENCE TO RELATED APPLICATIONS

This application is the U.S. national stage application of International Patent Application No. PCT/IB2012/053196, filed Jun. 25, 2012, which claims the benefit of U.S. Provisional Patent Application No. 61/500,809, filed Jun. 24,2011.

The Sequence Listing for this application is labeled "2HU6153.txt" which was created on Jun. 8, 2016 and is 34 KB. The entire content of the sequence listing is incorporated herein be reference in its entirety.

FIELD OF THE INVENTION

The present invention relates to substances and compositions thereof useful in the control of cancer stem cell persistence and concomitant tumor recurrence and/or control of tumor growth. In particular, the invention relates to substances and compositions useful in the treatment of cancers and/or tumors linked to cancer stem cells, in particular brain cancers and/or tumors, in a subject.

BACKGROUND OF THE INVENTION

One form of brain tumor, glioma, is the most frequent brain tumor in adults and, in its most malignant forms (astrocytoma grade IV or glioblastoma multiforme), represents some of the most aggressive cancers in man, with a 5-year survival rate of less than 5% (Reardon et al., 2006, *J. Clin. Oncol.,* 24, 1253). Gliomas are classified into subcategories according to their phenotypical resemblance to glial cells, mostly astrocytes (astrocytomas) or oligodendrocytes (oligodendrogliomas). Based on histopathological features, gliomas are also subdivided into low grade (grade I and II) and high grade (grade III and IV) tumors, which have distinct clinical prognoses (Reardon et al., 2006 , supra).

Glioblastoma multiforme (GBM) is a devastating invasive brain tumor able to give rise to many kinds of differentiated tumor cells. GBMs remain one of the most deadly cancers in adults, with an average period between diagnosis and death of ~12 months. GBM growth and persistence depend on cancer stem cells (Singh et al., 2003, *Cancer Res,* 63, 5821-5828; Singh et al., 2004, *Nature,* 432, 396-401) with enhanced DNA damage repair programs (Bao et al., 2006, *Nature,* 444, 756-760) that also induce recurrence and resist current chemo- and radio-therapies. This discovery provides a plausible explanation for the difficulty of GBM treatment and the high rate of relapse. Indeed, as GBM cells are highly invasive, surgery is not routinely curative. New strategies to target GBM stem cells are thus required. One key pathway implicated in the control of GBM growth and stemness is HH-GLI (Hedgehog-Gli) (Clement et al,. 2007, *Curr Biol,* 17, 165-172). This role of HH-GLI parallels its control of normal brain growth stem cell behavior (Palma and Ruiz i Altaba, 2004, *Development,* 131, 337-345). Interestingly, HH-GLI was shown to regulate a number of stemness genes, including NANOG (Stecca and Ruiz i Altaba, 2009, *Embo J,* 28, 663-676). The expression of the homeobox gene NANOG forms part of an Embryonic Stem (ES)-like stemness signature described in GBMs (Clement et al., 2007 , supra), later also found in other advanced cancer types (Ben-Porath et al., 2008, *Nat Genet,* 40, 499-507). However, it is not known if this signature in general, and NANOG in particular, have functional relevance in these tumors or their stem cells.

Thus, given the many suggested GLI1 downstream genes, there have not been demonstrated, until now, essential mediators that could provide additional intervention strategies to treat GBMs and other brain tumors and/or cancers.

The invention disclosed in the present application solves this problem by having identified a new target and mediator that has functional relevance in tumors and their cancer stem cells, particularly GBM tumors.

SUMMARY OF THE INVENTION

The present invention is based on the unexpected finding that the expression of the homeodomain protein NANOG depends on endogenous HH-GLI activity and its function is absolutely required for human GBM growth in vivo within the brains of recipient mice. Moreover, several lines of evidence are provided herewith in favor of a role not only in the control of tumor volume, but also in the control of GBM stem cell behaviour. Therefore, in addition to its use as a biomarker, the requirement of NANOG in GBMs, and its apparent highly restricted normal expression in adults, supports the view that blocking NANOG, directly or indirectly, will be beneficial in treating GBMs or other tumors and cancers, as well as tumors and cancers linked to cancer stem cells.

The main advantages of blocking NANOG rather than another target for the prevention, repression or treatment of tumors and cancers are as follows:

First, NANOG neutralization has the potential to eliminate rather than just compromise cancer stem cell activity (i.e. blocking NANOG stops rather than slows cancer stem cell activity, and, thus, tumor growth).

Second, NANOG appears to be expressed in few adult cells (such as germ cells). Therefore side effects in "normal tissues" should be minimized or absent.

Third, NANOG is a good candidate for combination therapies because it adds to, not necessarily replaces, current practices. Combination therapy is optimal for preventing resistance, since the cells missed by anti-NANOG therapy could be hit by the combination,and vice versa.

Therefore, a first aspect of the invention provides a NANOG antagonist for use in controlling cancer stem cell persistence and concomitant tumor recurrence, preferably for controlling cancer stem cell stemness, clonogenicity, proliferation and/or survival, and/or tumor growth in a subject.

A second aspect of the invention relates to a NANOG antagonist for use in the prevention, treatment or repression of cancers and/or tumors linked to cancer stem cells, preferably brain cancers and/or tumors including glioblastoma multiforme.

A third aspect of the invention relates to a use of a NANOG antagonist for controlling cancer stem cell persistence and concomitant tumor recurrence, preferably for controlling cancer stem cell stemness, clonogenicity, proliferation and/or survival, and/or tumor growth in a subject.

A fourth aspect of the invention relates to a use of a NANOG antagonist for the preparation of a pharmaceutical composition for preventing or treating cancers and/or tumors linked to cancer stem cells, preferably brain tumors and/or cancers, including glioblastoma multiforme, in a subject.

A fifth aspect of the invention is a pharmaceutical formulation comprising a NANOG antagonist and at least one pharmaceutically acceptable carrier.

A sixth aspect of the invention is a use of a NANOG polypeptide or a NANOG polypeptide fragment for the preparation of a pharmaceutical composition for preventing, repressing or treating cancers and/or tumors linked to cancer stem cells, preferably brain tumors and/or cancers, in a subject, wherein said polypeptide or polypeptide fragment induces an antibody response sufficient to neutralize or antagonize endogenous NANOG in said subject.

A seventh aspect of the invention relates to a method for controlling cancer stem cell persistence and concomitant tumor recurrence, preferably for controlling cancer stem cell stemness, clonogenicity, proliferation and/or survival, and/or tumor growth in a subject, said method comprising administering to a subject in need thereof an effective amount of a NANOG antagonist, or a pharmaceutical formulation thereof.

An eighth aspect of the invention relates to a method for controlling cancer stem cell persistence and concomitant tumor recurrence, preferably for controlling cancer stem cell stemness, clonogenicity proliferation and/or survival, and/or tumor growth in a subject, said method comprising administering to a subject in need thereof an amount of a NANOG polypeptide or a NANOG polypeptide fragment, or a pharmaceutical formulation thereof, sufficient to induce an antibody response sufficient to neutralize or antagonize endogenous NANOG or its function in said subject.

A ninth aspect of the invention is a method of preventing, repressing or treating cancers and/or tumors linked to cancer stem cells, preferably brain cancers and/or brain tumors, in a subject, said method comprising administering to a subject in need thereof a therapeutically effective amount of a NANOG antagonist, or a pharmaceutical formulation thereof.

A tenth aspect of the invention relates to a method of preventing, repressing or treating cancers and/or tumors linked to cancer stem cells, preferably brain cancers and/or brain tumors, in a subject, said method comprising administering to a subject in need thereof an amount of a NANOG polypeptide or a NANOG polypeptide fragment, or a pharmaceutical formulation thereof, sufficient to induce an antibody response sufficient to neutralize or antagonize endogenous NANOG in said subject.

Other features and advantages of the invention will be apparent from the following detailed description.

DETAILED DESCRIPTION OF THE INVENTION

Figure 1:
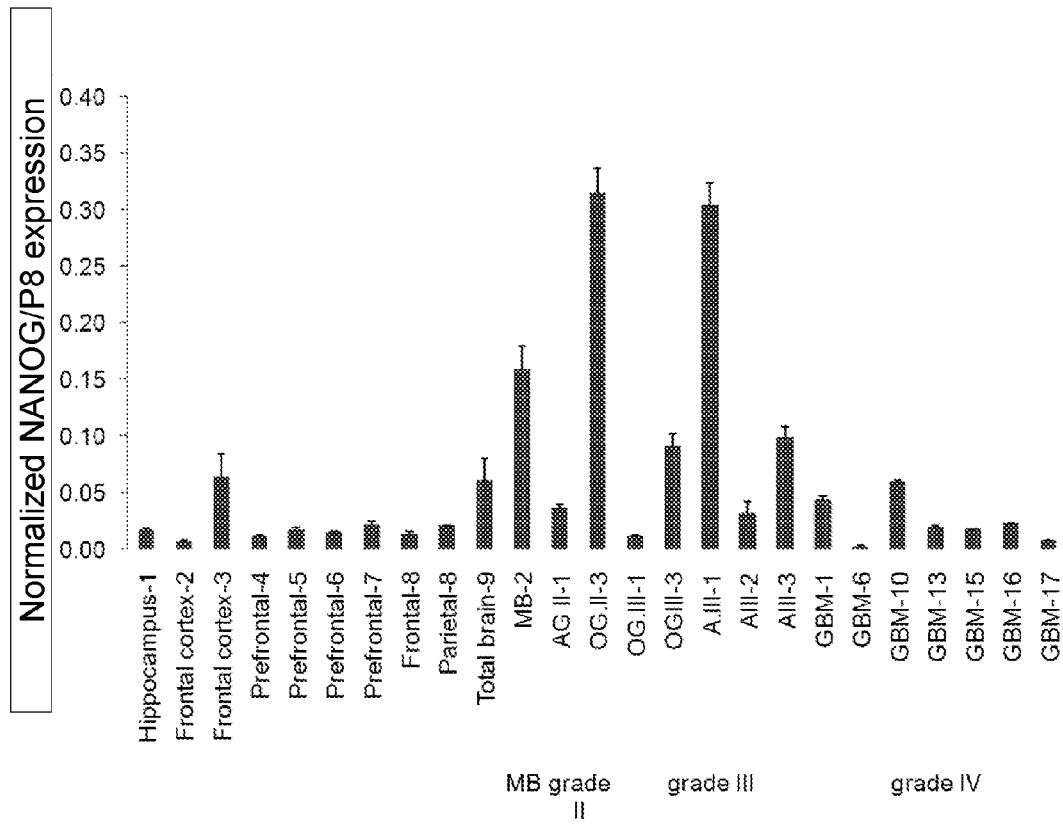
FIG. 1 shows the relative mRNA expression levels of NANOG/NANOGP8 in normal brain tissue, and in primary brain tumor cells obtained from WHO grade II, III, and IV (GBM) tumors. A: Astrocytoma; AG: Anaplastic glioma; GBM: Glioblastoma multiforme; OG: oligodendroglioma; MB: medulloblastoma. Roman numerals refer to WHO tumor grade. Arabic numerals refer to tumor sample.

The terms "NANOG", "NANOG protein", or "NANOG polypeptide", refer to mammalian or vertebrate NANOG protein, isoforms, dimers, oligomers, and fragments thereof. NANOG, also known as NANOG homeodomain protein, is a transcription factor critically involved with self-renewal of undifferentiated embryonic stem cells.

In particular, NANOG is a transcription regulator involved in inner cell mass and embryonic stem (ES) cell proliferation and self-renewal. It imposes pluripotency on ES cells and prevents their differentiation towards extraembryonic endoderm and trophectoderm lineages. It blocks bone morphogenetic protein-induced mesoderm differentiation of ES cells by physically interacting with SMAD 1 and interfering with the recruitment of coactivators to the active SMAD transcriptional complexes. It acts as a transcriptional activator or repressor. It binds optimally to the DNA consensus sequence 5'-[CG][GA][CG]C[GC]ATTAN[GC]-3' (SEQ ID NO: 34). When overexpressed, it promotes cells to enter into S phase and proliferation. In humans, NANOG is a polypeptide of 305 or 289 amino acids depending on the isoform. Human NANOG polypeptide is encoded by two coding genes: NANOG and NANOGP8 (Booth and Holland, 2004, *Genomics*, 84, 229-238). In humans, two variant alleles of NANOG are known (alleles a and b). NANOG and NANOGP8 genes are known in the art and their coding sequence can comprise the nucleic acid sequences as set forth in SEQ ID NO: 9 and SEQ ID NO: 10, respectively. Thus, as used herewith, "NANOG" includes, in particular, human NANOG which can be described by an amino acid sequence as set forth in SEQ ID NO: 1, SEQ ID NO: 2, SEQ ID NO: 3 or SEQ ID NO: 4. This term further encompasses a protein encoded by a nucleic acid sequence as set forth in SEQ ID NO: 9, SEQ ID NO: 10, or homologous sequences thereof, i.e. a variant nucleic acid sequence having at least 80%, at least 85%, at least 90%, at least 95%, at least 96%, at least 97%, at least 98% or at least 99% identical to SEQ ID NO: 9 or SEQ ID NO: 10. As used herein, the term NANOG also encompasses mouse NANOG (SEQ ID NO: 6), bovine NANOG (SEQ ID NO: 7) and rat NANOG (SEQ ID NO: 8). As used herein, the terms "NANOG", "NANOG protein", or "NANOG polypeptide" encompass polypeptides having an amino acid sequence such as those described above or fragments thereof comprising an amino acid sequence of SEQ ID NO: 5. In addition, the term "NANOG polypeptide" encompasses polypeptides that have a high degree of similarity or a high degree of identity with the amino acid sequence of SEQ ID NO: 1, SEQ ID NO: 2, SEQ ID NO: 3 or SEQ ID NO: 4, and which polypeptides are biologically active, i.e. said polypeptides mediate the acquisition of pluripotency or exhibit one of the functions attributed to NANOG (see NANOG definition above). In particular, the term "NANOG polypeptide" encompasses polypeptides substantially homologous to a polypeptide of SEQ ID NO: 1, SEQ ID NO: 2, SEQ ID NO: 3 or SEQ ID NO: 4, or an isoform or fragment thereof, e.g. which have an amino acid sequence different from that of native human NANOG or NANOG fragment because of one or more deletions, insertions or substitutions. "Substantially homologous" means a variant amino acid sequence that is at least 80%, at least 85%, at least 90%, at least 95%, at least 96%, at least 97%, at least 98% or at least 99% identical to the native amino acid sequences, as disclosed above. The percent identity of two amino acid or two nucleic acid sequences can be determined by visual inspection and/or mathematical calculation, or more easily by comparing sequence information using a known computer program used for sequence comparison such as Clustal package version 1.83. It further encompasses polypeptides which may comprise a sequence having at least one conservatively substituted amino acid, meaning that a given amino acid residue is replaced by a residue having similar physicochemical characteristics. In humans, NANOG protein mainly comprises a transcriptional interference domain composed of the 96 first amino acids at the N-terminus part, a DNA-binding homeodomain (also called herein "homeodomain") composed of 60 amino acids, and a transactivation domain composed of 101 amino acids at the C-terminus part. The nuclear localization signals (NLS) essential for NANOG activity as a transcription factor are within the homeodomain, while the nuclear export sequence (NES) is within the W (tryptophan-rich region) motif (SEQ ID NO: 35) involved in dimerization of NANOG (Chang et al, 2009, *Stem cells*, 27, 812-821). In humans, the NANOG homeodomain has the amino acid sequence of SEQ ID NO: 5, the tryptophan-rich region containing the nuclear export sequence (NES) and the dimerization domain has the amino acid sequence of SEQ ID NO: 35. The term "NANOG antagonist" or "NANOG inhibitor" as used herein refers to any substances that are able to totally or partially inhibit, block, attenuate, or interfere with NANOG, with the functional dimerization of NANOG, or with any pathway elicited, either directly or indirectly, by NANOG. Thus, the term "antagonists" is intended to include, but is not limited to, molecules which neutralize the effect of NANOG. For example, NANOG antagonists include substances which prevent, decrease or even eradicate the cancer stem cell populations which are at the origin of the tumor, tumor growth, recurrence and metastasis and, thus, which prevent, decrease or abolish tumor growth. For example, NANOG antagonists include small molecules, peptides, peptidomimetics, chimeric proteins, natural or unnatural proteins, nucleic acid derived polymers (such as DNA and RNA aptamers, siRNAs (small interfering RNAs), shRNAs (short hairpin RNAs), PNAs (Peptide Nucleic Acids), or LNAs (Locked Nucleic Acids), fusion proteins with NANOG antagonizing activities, antibody antagonists such as neutralizing anti-NANOG antibodies, or gene therapy vectors driving the expression of such NANOG antagonists. For example, NANOG antagonists include chimeric polypeptides acting as repressors of NANOG targets, in particular of NANOG positive targets, and, for instance, shutting down the expression of GLI1 and/or other NANOG positive targets such as KLF5 (Krueppel-like factor 5), COL4A6 (Collagen alpha-6(IV) chain), JUN (jun proto-oncogene), ID2 (DNA-binding protein inhibitor ID-2), SLC7A11 (Cystine/glutamate transporter), CSPG2 (chondroitin sulfate proteoglycan 2) or those described in Piestun et al. (2006, *J. Bioch. Biophys. Res. Comm.*, 343, P279-285). NANOG positive targets as defined herein relate to gene targets the expression of which is positively regulated by NANOG that acts as an activator. Chimeric polypeptides according to the invention include, for instance, NANOG dominant-negative polypeptides comprising the NANOG homeodomain fused to the repressor domain of a heterologous protein. As defined herein "NANOG homeodomain", or "DNA-binding homeodomain", encompasses the human NANOG homeodomain of amino acid sequence SEQ ID NO: 5, and polypeptides that have a high degree of similarity or a high degree of identity with the amino acid sequence of SEQ ID NO: 5, and which polypeptides are biologically active, i.e. said polypeptides bind to the DNA consensus sequence 5'-[CG][GA][CG]C[GC]ATTAN[GC]-3' (SEQ ID NO: 34) within the DNA region recognized by NANOG. In particular, it encompasses any polypeptide substantially homologous to the NANOG homeodomain of amino acid sequence SEQ ID NO: 5, or an isoform or fragment thereof, e.g. which has an amino acid sequence different from that of the native human NANOG homeodomain because of one or more deletions, insertions or substitutions. "_Substantially homologous⁻" means a variant amino acid sequence that is at least 80%, at least 85%, at least 90%, at least 95%, at least 96%, at least 97%, at least 98% or at least 99% identical to the native amino acid sequence of the NANOG homeodomain, as disclosed above. It further encompasses polypeptides which may comprise a sequence having at least one conservatively substituted amino acid, meaning that a given amino acid residue is replaced by a residue having similar physicochemical characteristics. Any repressor domain of a heterologous protein can be included in the chimeric polypeptide according to the invention. The repressor domain can be selected, for instance, from the repressor domain of an Engrailed protein (such as SEQ ID NO: 36 and SEQ ID NO: 38), the repressor domain of Pit-1beta (SEQ ID NO: 37), the repressor domain of IRF 1 (SEQ ID NO: 39), and the WRPW motif of the hairy related protein (Fisher et al., 1996, *Mol. Cell. Biol.* 16(6): 2670-2677) (SEQ ID NO: 44).

The term "NANOG dominant-negative protein" or "NANOG dominant-negative polypeptide" refers to a chimeric polypeptide that partially or totally inhibits, blocks, attenuates, or interferes with the transcription or general expression of any NANOG target, including GLI1.

The term "NANOG antibody" or "anti-NANOG antibody" as used herein refers to any antibody or variant form thereof, including, but not limited to, an antibody fragment, domain antibody or single chain antibody capable of selectively binding to NANOG protein or fragments thereof. In particular, NANOG antibodies include a NANOG antibody able to bind to the epitopes of mammalian, notably human, NANOG, in particular NANOG of amino acid sequence SEQ ID NO: 1, SEQ ID NO: 2, SEQ ID NO: 3 and/or SEQ ID NO: 4, or in particular epitopes localized within a region consisting of amino acid sequence SEQ ID NO: 5. A NANOG antibody includes murine, chimeric, humanized, or fully human antibodies, genetically engineered or bispecific or multispecific antibodies as well as fragments thereof such as single chain antibodies (scFv) or domain antibodies against NANOG protein or fragments thereof and the like. Antibodies of this invention may be monoclonal or polyclonal antibodies, or fragments or derivatives thereof having substantially the same antigen specificity. The term "selectively" indicates that the antibodies preferentially recognize and/or bind to the target polypeptide or epitope, i.e., with a higher affinity than to any other antigen or epitope, i.e. the binding to the target polypeptide can be discriminated from non-specific binding to other antigens. The binding affinity of an antibody can be readily determined by one of ordinary skill in the art, for example, by Scatchard analysis (Scatchard et al., 1949, *Ann. N.Y. Acad.,* 1949, 51, 660-672).

The term "antibody antagonists" as used herein refers to any antibody or variant form thereof, including, but not limited to, an antibody fragment, domain antibody or single chain antibody capable of reducing the activity of a given pathway, enzyme, receptor or ligand, such as a NANOG pathway. Antibody antagonists include antibodies in a conventional immunoglobulin format (IgA, IgD, IgE, IgG, IgM), and also fragments thereof or any other "antibody-like" format that binds to human NANOG (for example, a single chain Fv fragment, a fragment Fc, a Fd fragment, a Fab fragment, a Fab' fragment, a F(ab)$_2$ fragment, chimeric antibodies, diabodies, domain antibodies (dAbs) such as described in Holliger et al. (2005, *Nature Biotechnology,* 23(9), 1126-1136) and polypeptides that contain at least a portion of an immunoglobulin that is sufficient to confer specific antigen-binding to the polypeptide (e.g., inmmunoadhesins). The terms Fv, Fe, Fd, Fab, or F(ab)$_2$ are used with their standard meanings (Harlow et al., 1988, *Antibodies: A Laboratory Manual, Cold Spring Harbor Laboratory Press*; Dec. 1, 1988 . ISBN 978-0879693145). In the sense of the invention, the term "antibody antagonists" comprises an antibody as defined herewith fused to a compound capable of crossing the blood-brain barrier, for example a peptide such as the transferrin-like peptide of amino acid sequence CRTIGPSVC (SEQ ID NO: 41) (Staquicini et al., 2011, *Clin. Invest.,* 121 (1):161-173), so as to facilitate access to the brain tumor site.

The term "monoclonal antibody" as used herein refers to an antibody obtained from a population of substantially homogeneous antibodies, i.e., the individual antibodies comprising the population are identical except for possible naturally occurring mutations that may be present in some minor amounts. Monoclonal antibodies are highly specific, as being directed against a single antigenic site. The modifier term "monoclonal" indicates the character of the antibody as being obtained from a substantially homogeneous population of antibodies, and is not to be construed as requiring production of the antibody by any particular method.

The term "humanized antibody" refers to a type of engineered antibody having its CDRs derived from a non-human donor immunoglobulin, the remaining immunoglobulin being derived from one or more human or non-immunogenic to humans immunoglobulin(s). In addition, framework support residues may be altered to preserve binding affinity of the donor immunoglobulin (Queen et al., 1989, *Proc. Natl. Acad. Sci. USA,* 86:10029-10032).

The term "donor antibody" refers to a non-human antibody which contributes the amino acid sequences of its variable regions, CDRs, or other functional fragments or analogues thereof to the humanized antibody, and thereby provides the humanized antibody with the antigenic specificity and neutralizing activity characteristic of the donor antibody. A suitable donor antibody may be selected by methods as described in *Handbook of Therapeutic Antibodies*. Stefan Dübel (Ed.) January 2007. ISBN. 978-3-527-31453-9.

The term "acceptor antibody" refers to an antibody heterologous to the donor antibody, which provides the amino acid sequences of its heavy and/or light chain framework regions and/or its heavy and/or light chain constant regions to the humanized antibody. The acceptor antibody may be derived from any mammal provided that it is non-immunogenic in humans. Preferably, the acceptor antibody is a human antibody. A suitable human acceptor antibody may be selected for its homology to the nucleotide and amino acid sequences of the donor antibody. For example, a suitable human acceptor antibody may be found by methods as described in *Handbook of Therapeutic Antibodies*. Stefan Dübel (Ed:) January 2007. ISBN: 978-3-527-31453-9.

Antibodies according to the invention can be generated by immunization of a suitable host (e.g., vertebrates, including humans, mice, rats, sheep, goats, pigs, cattle, horses, reptiles, fish, amphibians, and eggs of birds, reptiles and fish). Determination of immunoreactivity with an immunogenic NANOG polypeptide may be made by any of several methods well known in the art, including, e.g., immunoblot assay and ELISA (Enzyme-Linked Immunosorbent Assay). Modification of such antibodies into therapeutically useful derivatives may be made by methods as described in *Handbook of Therapeutic Antibodies*. Stefan Dübel (Ed:) January 2007. ISBN: 978-3-527-31453-9.

The term "CDRs" refers to the complementarity determining region amino acid sequences of an antibody which are the hypervariable regions of immunoglobulin heavy and light chains. It refers to all three heavy chain CDRs, and/or all three light chain CDRs.

The term "anti-NANOG antibody" may be a neutralizing anti-NANOG antibody or a fragment thereof, such as a murine antibody, a humanized antibody such as a humanized variant of a murine antibody, a human antibody, or a fragment thereof. A non-limiting list of examples of anti-NANOG antibody include known commercial antibodies such as: anti-human NANOG antibodies produced in mouse (Sigma: WH0079923M1, SAB1405280, N3038; Cell Signaling: 4893; Novus: H00079923-M08, NBP1-47427, H00079923-MO2, H00079923-M04, H00079923-M01, H00079923-M09, NBP1-43304), anti-human NANOG antibody produced in rabbit (Sigma: AV100591, SAB2104004, SAB2104002, SAB3500389; Cell Signaling: 4903, 5448, 5232, 3580; Origene: TA307042, TA302154, TA302153, TA306915; Novus: 29290002 , NB100-93546, NB110-40414, NBP1-55260, NBP1-41038; Epitomics: 3369-1, 4561-1, 4562-1), anti-human NANOG antibodies produced in goat (Sigma: SAB2500671, SAB2500670; R&D: AF1997, BAF1997, NL1997G, NL493, IC1997P; Origene: TA303206, TA303048; Novus: NB110-40660, NB100-59737), anti-mouse NANOG antibodies produced in goat (R&D: AF2729, BAF272), anti-mouse NANOG antibodies produced in rabbit (Novus: NB100-587), anti-human, mouse, and rat NANOG antibodies produced in rabbit (Sigma: N4413); anti-human and mouse NANOG antibodies produced in rabbit (Millipore, AB9220; Novus: NB100-588), anti-human and mouse NANOG antibodies produced in mouse (Novus: NBP1-04320), anti-human and rat NANOG antibodies produced in mouse (Millipore, MAB 10091), rat mAb (monoclonal antibodies) such as R&D#1997 , goat antibodies such as R&D#1997; rabbit antibodies such as AbCam#ab21603 , AbCam#21624 , Cell Signaling#3580 and Kamiya rabbit#PC-102; mouse mAb such as Sigma#N3038; and humanized variants thereof.

In a still further embodiment, an anti-NANOG antibody according to the invention is a neutralizing anti-NANOG antibody as mentioned above fused to a compound capable of crossing the blood-brain barrier, for example a peptide such as the transferrin-like peptide of amino acid sequence SEQ ID NO: 41 (Staquicini et al., 2011).

The term "small inhibitory nucleic acids" (siNAs) refers to short nucleic acids used in strategies targeting mRNA recognition and its downregulation based on their antisense action. This term covers antisense oligonucleotides, catalytic nucleic acids such as ribozymes and deoxyribozymes, as well as small interfering RNAs (siRNAs).

The term "siRNAs" refers to small interfering RNAs which are single or double stranded RNAs (about 19-23 nucleotides) able to knock down or silence a targeted mRNA from a target gene. Artificial siRNAs can be either chemically synthesized as oligonucleotides or cloned into a plasmid or a virus vector (adenovirus, retrovirus or lentivirus) as short hairpin RNAs (shRNAs) to generate a transient or stable transfection in any type of cells (Martin et al., 2007, Ann. Rev. Genomics Hum. Genet., 8:81-108; Kolfschoten et al., 2007, Nat. Clin. Tract. Endocrinol. Metab., 3(12):827-34; Huang et al., 2008, Expert. Opin. Ther. Targets, 12(5), 637-645).

The term "peptidomimetic" is defined as a peptide analog containing non-peptidic structural elements, which peptide is capable of mimicking or antagonizing the biological action(s) of a natural parent peptide. A peptidomimetic lacks classical peptide characteristics such as enzymatically scissile peptide bonds.

A NANOG protein, as an isolated, purified or homogeneous protein according to the invention, may be produced by recombinant expression systems as described in Hart et al. (Dev. Dyn. 2004, 230(1):187-98).

Suitable systems of expression of NANOG, NANOG variants or fragments, or NANOG antagonists include transfected E. Coli.

The term "pharmaceutically acceptable" refers to a carrier comprised of a material that is not biologically or otherwise undesirable.

The term "carrier" refers to any components present in a pharmaceutical formulation other than the active agent and thus includes diluents, binders, lubricants, disintegrants, fillers, coloring agents, wetting or emulsifying agents, pH buffering agents, preservatives and the like.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it for example based on familial history; (b) inhibiting the disease, i.e., arresting its development; (c) or relieving the disease, i.e., causing regression of the disease and/or its symptoms or conditions such as improvement or remediation of damage.

In particular, treatment of tumors and/or cancers linked to cancer stem cells, for instance brain tumors and/or cancers, comprises preventing, decreasing or even eradicating the cancer stem cell populations which are at the origin of the tumor, tumor growth, recurrence and metastasis, for instance by controlling, reducing or inhibiting cancer stem cell persistence, e.g. proliferation and/or clonogenicity, and concomitant tumor recurrence. It also comprises preventing, decreasing or abolishing tumor growth.

The term "cancers and/or tumors linked to cancer stem cells" is defined herewith as cancers and/or tumors in which cancer stem cells have been demonstrated or are believed to be implicated. Non-limitative examples of cancers and tumors linked to cancer stem cells include hematopoietic cancers, brain cancer, breast cancer, colorectal cancer, head and neck cancer, pancreatic cancer, lung cancer, liver cancer, melanoma, prostate cancer, muscle cancer and mesenchymal cancer.

The term "cancer stem cells" refers to a subset of cancer-initiating cells that have the ability to self-renew and generate diverse cells that comprise the tumor. The cancer stem cells exhibit classic stem-like properties, including the possession of stem cell markers (Klonisch et al., 2008. Trends in Molecular Medicine 14 (10):450-460) and are able to continually initiate and sustain tumorigenesis and/or reinitiate tumorigenesis in the same site after incomplete therapeutic ablation or elsewhere during metastases.

The term "brain tumor" is defined herewith as an intracranial solid neoplasm or tumor (defined as an abnormal growth of cells) within the brain or the central spinal canal. Brain tumors include all tumors inside the cranium or in the central spinal canal. They are created by an abnormal and uncontrolled cell division, normally either in the brain itself (neurons, glial cells (astrocytes, oligodendrocytes, ependymal cells, myelin-producing Schwann cells), lymphatic tissue, blood vessels), in the cranial nerves, in the brain envelopes (meninges), skull, pituitary and pineal gland, or spread from cancers primarily located in other organs (metastatic tumors). Brain tumors cover, for example, human gliomas including glioblastoma multiforme, schwanommas, metastasis to the brain, meningiomas, ependymomas, lower-grade gliomas and medulloblastomas.

The term "subject" as used herein refers to mammals. For example, mammals contemplated by the present invention include humans, primates, domesticated animals such as cattle, sheep, pigs, and horses, laboratory rodents and the like.

The term "efficacy" of a treatment or method according to the invention can be measured based on changes in the course of a disease or condition in response to a use or a method according to the invention. For example, the efficacy of a treatment or method according to the invention can be measured by a reduction of tumor volume, and/or an increase of progression free survival time, and/or a decreased risk of relapse post-resection for primary cancer.

The term "effective amount" as used herein refers to an amount of at least one NANOG antagonist or a pharmaceutical formulation thereof according to the invention that elicits a detectable reduction of cancer stem cell persistence and concomitant tumor recurrence, e.g. cancer stem cell stemness, clonogenicity, proliferation and/or survival, and/or a reduction in the volume of the tumor in a subject that is being administered said NANOG antagonist.

The term "recurrence" means the ability of a cancer to reappear due to the ability of stem cells to survive, to maintain their intrinsic properties (e.g. clonogenicity), their survival and proliferation ability and optionally to maintain further properties (e.g. differentiation ability as measured by expression of differentiation markers, stemness properties as measured by expression of stemness markers and metabolic properties) after treatment by an agent such as a NANOG antagonist according to the invention. Measurement of recurrence is performed by clinical neurological observation and imaging for tumor mass. The recurrence level will be evaluated on the basis of the proportion of surviving brain cancer mass after treatment during the recovery period and on the length of the recovery period during which no recurrence of brain cancer mass is observed.

The term "an antibody response sufficient to neutralize or antagonize endogenous NANOG" refers to a protective immune response against NANOG activity, e.g. an induction of the production of circulating antibodies that neutralize endogenous NANOG and/or an antibody response that prevents, represses or treats tumor development, in particular brain tumor development, or controls, reduces or inhibits cancer stem cell persistence and concomitant tumor recurrence, in particular brain cancer stem cell clonogenicity and/or proliferation, in a subject. For example, subjects in which a protective immune response has been induced can exhibit reduced tumor growth and/or reduced risk of developing a tumor as compared to non-immunized control subjects.

NANOG antagonists

NANOG antagonists include substances described in the detailed description.

In a particular embodiment, a NANOG antagonist according to the invention is a neutralizing anti-NANOG antibody.

In a still further embodiment, a NANOG antagonist is a neutralizing anti-NANOG antibody as mentioned above fused to a compound capable of crossing the blood-brain barrier, for example a peptide such as the transferrin-like peptide of amino acid sequence SEQ ID NO: 41.

In a particular embodiment, a NANOG antagonist according to the invention is a small inhibitory nucleic acid with NANOG antagonizing activities, preferably a mature siRNA or a short hairpin RNA (shRNA) with NANOG antagonizing activities. Examples of shRNAs suitable as NANOG antagonists according to the invention include shNANOG1 of nucleotide sequence SEQ ID NO: 11, shNANOG2 of nucleotide sequence SEQ ID NO: 12, and shNANOGP8 of nucleotide sequence SEQ ID NO: 13.

Alternatively, NANOG antagonists can be generated in vivo in the form of autoantibodies, through the administration of a NANOG polypeptide or fragment thereof or a pharmaceutical composition thereof capable of inducing an antibody response sufficient to neutralize or antagonize endogenous NANOG in a subject. In this case, either intact NANOG, fragments thereof, or preferably synthetic peptides corresponding to epitopes of NANOG could be used as immunogens to elicit an immune response and the production of neutralizing autoantibodies against endogenous NANOG in a subject suffering from a brain tumor or cancer. Therapeutic levels of circulating neutralizing anti-NANOG autoantibodies could be maintained and controlled by appropriate immunization/booster protocols. A useful precedent is the use of immunization against certain endogenous fertility hormones such as LHRH (luteinizing hormone releasing hormone) and hCG (human chorionic gonadotropin) as methods of fertility regulation, contraception (Talwar, 1997, *Human Reproduction Update*, 3(4), 301-310; Talwar et al., 1994, *Proc. Natl. Acad. Sci. USA.*, 91, 8532-8536; Amato et al., 2002, *J. Clin. Endocr. & Metab.*, 87(3), 993-997) and treatment of hormone-dependent cancers (Conry et al., 2000, *Clinical Cancer Research*, 6, 34-41). These methods described in the above references hereby incorporated by reference in their entirety have been proven both effective and reversible in clinical trials. According to another aspect, a composition is provided comprising a NANOG polypeptide or fragment thereof capable of inducing an antibody response sufficient to neutralize or antagonize endogenous NANOG in a subject.

In an alternative embodiment, a NANOG antagonist is a chimeric polypeptide. In particular, the chimeric polypeptides according to the invention act as repressors of NANOG targets, in particular NANOG positive targets, and, for instance, shut down the expression of GLI1 and/or other NANOG positive targets in a context-dependent manner such as KLF5, COL4A6, JUN, ID2, SLC7A11, CSPG2 or those described in Piestun et al. (2006, *J. Bioch. Biophys. Res. Comm.*, 343. P279-285).

In a further embodiment, a NANOG antagonist is a chimeric polypeptide that is a NANOG dominant-negative polypeptide comprising a NANOG homeodomain fused to the repressor domain of a heterologous protein. According to a particular aspect of the invention,the NANOG homeodomain has the amino acid sequence SEQ ID NO: 5 or any amino acid sequence substantially homologous to SEQ ID NO: 5 that binds to the DNA consensus sequence 5'-[CG][GA][CG]C[GC]ATTAN[GC]-3' (SEQ ID NO: 34).

In a still further particular embodiment, in addition to the DNA-binding homeodomain, other parts of the NANOG protein are also included in the NANOG dominant-negative polypeptide of the invention, such as the dimerization domain (SEQ ID NO: 35)or a mutated dimerization domain in which the nuclear export sequence has been mutated to become non-functional while the W motifs are maintained to allow the dimerization function.

In a further embodiment, the NANOG dominant-negative polypeptide according to the invention can further comprise a targeting domain comprising one or more of the following, or any combination thereof:

(i) A cell penetrating peptide for translocating the chimeric polypeptide across the cell membrane, such as penetratin from Antennapedia of SEQ ID NO: 40 (Thoren et al., 2000, *FEBS Lett.*, 482, 265-268) that also crosses the blood-brain barrier;

(ii) A brain tumor targeting peptide, in particular for glioma targeting, such as the transferrin-like peptide of SEQ ID NO: 41 (Staquicini et al., 2011, *J. Clin. Investigation*, 121 (1), 161-173).

In a specific aspect of this embodiment, the NANOG dominant-negative polypeptide according to the invention further comprises a disulfide bond between the cell penetrating peptide and the brain tumor targeting peptide.

The NANOG homeodomain contains 2 functional nuclear localization signals (NLS) (Chang et al., 2009, *Stem Cells*, 27, 812-821). Therefore, a NANOG dominant-negative polypeptide according to the invention having no additional cell penetrating peptide, nor brain tumor targeting peptide, could be internalized in brain tumor cells and shut down NANOG positive targets in these cells.

Particularly advantageous for carrying out experimental testing of the NANOG dominant-negative polypeptides according to the invention is the further addition of a Tag, such as FLAG (SEQ ID NO: 42) or HA (SEQ ID NO: 43), for instance at the N terminal part or the C-terminal part of the chimeric polypeptide, to allow immunodetection of the chimeric polypeptides in cells, as well as their purification through antibody affinity chromatography.

Any repressor domain of a heterologous protein can be included in the NANOG dominant-negative polypeptide according to the invention. In a particular embodiment, the repressor domain is selected, for instance, from the repressor domain of Pit-1beta (SEQ ID NO: 37), the repressor domain of an Engrailed protein (such as SEQ ID NO: 36 or SEQ ID NO: 38), the repressor domain of IRF1 (SEQ ID NO: 39), and the WRPW motif of the hairy-related protein (SEQ ID NO: 44).

The chimeric polypeptides of the invention, and in particular the NANOG dominant-negative polypeptide according to the invention, are preferably able to be internalized in vivo into tumor cells and shut down GLI1 and other NANOG positive targets in the tumor cells, in particular in glioblastoma.

Chimeric proteins, and in particular a NANOG dominant-negative polypeptide, according to the invention can be administered systemically or locally by direct infusion into the brain through cannulas or in wafers following the operation to remove the tumor bulk (when possible).

In a further embodiment, a NANOG antagonist is a nucleic acid encoding a chimeric polypeptide as described herein, and in particular gene therapy vectors driving the expression of such chimeric polypeptides.

In a still further embodiment, a NANOG antagonist is a gene therapy vector driving the expression of a NANOG dominant-negative polypeptide as defined herein.

Compositions

The invention provides NANOG antagonists, NANOG polypeptides or fragments thereof, pharmaceutical compositions thereof, and methods for treating a subject, preferably a mammalian subject, and most preferably a human patient who is suffering from a medical disorder selected from cancers and/or tumors linked to cancer stem cells, preferably brain cancers and/or brain tumors, in particular glioblastoma multiforme (GBM).

In an alternative aspect, the invention provides NANOG antagonists, NANOG polypeptides or fragmentd thereof, pharmaceutical compositions thereof, and methods for treating a subject as described herein, wherein the subject is suffering from cancers and/or tumors linked to cancer stem cells selected from the group consisting of hematopoietic cancers, brain cancer, breast cancer, colorectal cancer, head and neck cancer, pancreatic cancer, lung cancer, liver cancer, melanoma, prostate cancer, muscle cancer and mesenchymal cancer.

According to another aspect, the invention provides NANOG antagonists, pharmaceutical compositions thereof and methods for controlling cancer stem cell persistence and concomitant tumor recurrence, preferably for controlling cancer stem cell stemness, clonogenicity, proliferation and/or survival, and/or for controlling tumor growth in a subject.In a preferred aspect, the NANOG antagonists, pharmaceutical compositions thereof and methods of the invention are for controlling brain cancer stem cell persistence and concomitant tumor recurrence as defined herein and/or for controlling brain tumor growth in a subject.

In a particular embodiment, the invention provides a pharmaceutical formulation according to the invention for use as a medicament.

Pharmaceutical compositions of the invention can contain at least one NANOG antagonist according to the invention in any form described herein. Compositions of this invention may further comprise one or more pharmaceutically acceptable additional ingredient(s) such as alum, stabilizers, antimicrobial agents, buffers, coloring agents, flavoring agents, adjuvants, and the like.

The compositions according to the invention, together with a conventionally employed adjuvant, carrier, diluent or excipient, may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use by injection or continuous infusion. Injectable compositions are typically based upon injectable sterile saline or phosphate-buffered saline or other injectable carriers known in the art. Such pharmaceutical compositions and unit dosage forms thereof may comprise ingredients in conventional proportions, with or withoutadditional active compounds or principles, and such unit dosage forms may contain any suitable effective amount of the active ingredient commensurate with the intended daily dosage range to be employed. According to a particular embodiment, compositions according to the invention are injectable.

Compositions of this invention may be liquid formulations including, but not limited to, aqueous or oily suspensions, solutions, emulsions, syrups, and elixirs. The compositions may also be formulated as a dry product for reconstitution with water or other suitable vehicle before use. Such liquid preparations may contain additives including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethyl cellulose, carboxymethyl cellulose, aluminum stearate gel, and hydrogenated edible fats. Emulsifying agents include, but are not limited to, lecithin, sorbitan monooleate, and acacia. Preservatives include, but are not limited to, methyl or propyl p-hydroxybenzoate and sorbic acid. Dispersing or wetting agents include but are not limited to poly(ethylene glycol), glycerol, bovine serum albumin, Tween®, Span®.

Further materials as well as formulation processing techniques and the like are set out in Part 5 of *Remington's Pharmaceutical Sciences*, 21$^{st}$ Edition, 2005, University of the Sciences in Philadelphia, Lippincott Williams & Wilkins, the content of which is incorporated herein by reference.

Compositions of this invention may also be formulated as a depot preparation, which may be administered by implantation or by intramuscular injection.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, acacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Compositions of this invention may also be formulated for inhalation, which may be in a form including, but not limited to, a solution, suspension, or emulsion that may be administered as a dry powder or in the form of an aerosol using a propellant.

The compounds of this invention can also be administered in sustained release forms or from sustained release drug delivery systems. A description of representative sustained release materials can also be found in the incorporated materials in *Remington's Pharmaceutical Sciences*.

In a particular embodiment, when the NANOG antagonist according to the invention is a small inhibitory nucleic acid, in particular a siRNA, it may be advantageously delivered in encapsulated form into nanoparticles or liposomes such as described in Fenske et al., 2008, *Expert Opin, Drug Deliv.,* 5(1), 25-44; de Fougerolles, 2008, *Hum. Gene Ther.,* 19(2), 125-32; Huang et al., 2008, above, the contents of which are herein incorporated by reference in their entirety.

In a particular aspect, the composition to be administered to a subject in order to induce an antibody response sufficient to neutralize or antagonize endogenous NANOG may, optionally, contain an adjuvant and may be delivered in any manner known in the art for the delivery of immunogen to a subject.

According to another embodiment, a pharmaceutical formulation according to the invention is provided wherein the NANOG antagonist is a neutralizing anti-NANOG antibody.

In a still further embodiment, a pharmaceutical formulation according to the invention, is provided wherein the NANOG antagonist is a neutralizing anti-NANOG antibody as mentioned above fused to a compound capable of crossing the blood-brain barrier, for example a peptide such as the transferrin-like peptide of amino acid sequence SEQ ID NO: 41.

The dosage administered, as single or multiple doses, to an individual will vary depending upon a variety of factors, including pharmacokinetic properties, subject conditions and characteristics (sex, age, body weight, health, size), extent of symptoms, concurrent treatments, frequency of treatment and the effect desired.

According to another particular aspect, compositions according to the invention further comprise a compound that enhances the uptake of the antagonist according to the invention by brain tumor cells of the subject, such as the transferrin-like peptide of amino acid sequence SEQ ID NO: 41.

Mode of Administration

Compositions of this invention may be administered in any manner including intravenous injection, intra-arterial, intraperitoneal injection, subcutaneous injection, intramuscular, intra-thecal, oral route, cutaneous application, direct tissue perfusion during surgery or combinations thereof.

The compositions of this invention may also be administered in the form of an implant, which allows slow release of the compositions as well as a slow controlled i.v. infusion.

Delivery methods for the composition of this invention include known delivery methods for anti-cancer drugs such as intra-venal peripheral injection, intra-tumoral injection or any type of intracranial delivery such as convection enhanced delivery (CED) (Bobo et al., 1994, *PNAS,* 91 (6), 2076-2080; Lino et al., 2009, *Curr. Opin. Cell Biol.,* 21, 311-316).

Combination

According to the invention, the NANOG antagonist, the NANOG polypeptide or fragment thereof used to generate NANOG auto-antibodies, and pharmaceutical formulations thereof can be administered alone or in combination with a co-agent useful in the treatment of cancers and/or tumors, preferably brain cancers and/or tumors, in particular glioblastoma multiforme, such as substances useful for preventing cell proliferation and/or cell survival, for example a co-agent selected from bevacizumab, temazolomide, procarbazine, carmustine, and cilengitide, and/or substances useful for reducing the blood brain barrier effect, for example the transferrin-like peptide of amino acid sequence SEQ ID NO: 41.

The invention encompasses the administration of a NANOG antagonist and pharmaceutical formulations thereof, or of a NANOG polypeptide or fragment thereof used to generate NANOG auto-antibodies, wherein the NANOG antagonist or pharmaceutical formulation thereof, or the NANOG polypeptide or fragment thereof used to generate NANOG auto-antibodies, is administered to an individual prior to, simultaneously or sequentially with other therapeutic regimens or co-agents useful in the treatment of cancers and/or tumors, preferably brain cancers and/or brain tumors, in particular glioblastoma multiforme, (e.g. multiple drug regimens), in a therapeutically effective amount.

The invention also encompasses the administration of a NANOG antagonist and pharmaceutical formulations thereof, or of a NANOG polypeptide or fragment thereof used to generate NANOG auto-antibodies, wherein the NANOG antagonist or pharmaceutical formulation thereof, or the NANOG polypeptide or fragment thereof used to generate NANOG auto-antibodies, is administered to an individual simultaneously with other co-agents useful for reducing the blood brain barrier effect, for example the transferrin-like peptide of amino acid sequence SEQ ID NO: 41, in a therapeutically effective amount.

A NANOG antagonist or the pharmaceutical formulation thereof, or the NANOG polypeptide or fragment thereof used to generate NANOG auto-antibodies, that is administered simultaneously with said co-agents can be administered in the same or different composition(s) and by the same or different route(s) of administration.

According to one embodiment, a pharmaceutical formulation is provided comprising a NANOG antagonist, combined with at least one co-agent useful in the treatment of cancers and/or tumors, preferably brain cancers and/or brain tumors, in particular glioblastoma multiforme, and at least one pharmaceutically acceptable carrier.

Subjects

In an embodiment, subjects according to the invention are subjects suffering from cancers and/or tumors linked to cancer stem cells, preferably brain cancers and/or brain tumors.

In another embodiment, subjects according to the invention are subjects suffering from glioblastoma multiforme.

In another embodiment, subjects according to the invention are subjects suffering from glioma, astrocytoma, medulloblastoma, epedymoma or oligodendroglioma.

In another embodiment, subjects according to the invention are subjects suffering from hematopoietic cancers, brain cancer, breast cancer, colorectal cancer, head and neck cancer, pancreatic cancer, lung cancer, liver cancer, melanoma, prostate cancer, muscle cancer and mesenchymal cancer.

In a further embodiment, subjects according to the invention are subjects suffering from metastatic and non-metastatic cancers such as rectal cancer, renal cell carcinoma, ovarian cancer, prostate cancer, bone cancer, bone metastasis, leukemias, testicular cancer, uterine cancers, cervical cancers, endometrial cancer or other cancers responsive to therapy using NANOG antagonists.

Use according to the invention

In one embodiment of the invention a use of a NANOG antagonist is provided for the preparation of a pharmaceutical composition for controlling cancer stem cell persistence and concomitant tumor recurrence, in particular for controlling cancer stem cell stemness, clonogenicity, proliferation and/or survival, and/or for controlling tumor growth, in a subject.

In a preferred aspect of this embodiment a use of a NANOG antagonist is provided for the preparation of a pharmaceutical composition for controlling brain cancer stem cell persistence and concomitant tumor recurrence, in particular for controlling brain cancer stem cell stemness, clonogenicity, proliferation and/or survival, and/or brain tumor growth in a subject.

In another embodiment of the invention a use of a NANOG antagonist is provided for the preparation of a pharmaceutical composition for the prevention, repression or treatment of cancers and/or tumors linked to cancer stem cells, preferably cancers and/or tumors selected from the group consisting of haematopoetic cancers, brain cancer, breast cancer, colorectal cancer, head and neck cancer, pancreatic cancer, lung cancer, liver cancer, melanoma, prostate cancer, muscle cancer and mesenchymal cancer.

In a preferred aspect of the invention, a use of a NANOG antagonist is provided for the preparation of a pharmaceutical composition for the prevention, repression or treatment of brain cancers and/or brain tumors.

In a still preferred aspect, a use of a NANOG antagonist is provided for the preparation of a pharmaceutical composition for the prevention, repression or treatment of glioblastoma multiforme.

In another embodiment of the invention a method is provided for controlling cancer stem cell persistence and concomitant tumor recurrence, in particular for controlling cancer stem cell stemness, clonogenicity, proliferation and/or survival, and/or for controlling tumor growth, in a subject, said method comprising administering to a subject in need thereof an effective amount of a NANOG antagonist, or a pharmaceutical formulation thereof.

In a preferred aspect of the above embodiment, cancer stem cells are from cancers and/or tumors selected from the group consisting of hematopoietic cancers, brain cancer, breast cancer, colorectal cancer, head and neck cancer, pancreatic cancer, lung cancer, liver cancer, melanoma, prostate cancer, muscle cancer and mesenchymal cancer.

In a still preferred aspect of the invention a method is provided for controlling brain cancer stem cell persistence and concomitant tumor recurrence, in particular for controlling brain cancer stem cell stemness, clonogenicity, proliferation and/or survival, and/or for controlling brain tumor growth, in a subject, said method comprising administering to a subject in need thereof an effective amount of a NANOG antagonist, or a pharmaceutical formulation thereof.

In another embodiment a method is provided of preventing, repressing or treating cancers and/or tumors linked to cancer stem cells, preferably cancers and/or tumors selected from the group consisting of hematopoietic cancers, brain cancer, breast cancer, colorectal cancer, head and neck cancer, pancreatic cancer, lung cancer, liver cancer, melanoma, prostate cancer, muscle cancer and mesenchymal cancer, more preferably brain cancer and/or tumor, in a subject, said method comprising administering to a subject in need thereof a therapeutically effective amount of a NANOG antagonist, or a pharmaceutical formulation thereof.

In another embodiment of the invention a use is provided of a NANOG polypeptide or a NANOG polypeptide fragment, typically a synthetic polypeptide corresponding to epitopes of NANOG, for the preparation of a pharmaceutical composition for controlling cancer stem cell persistence and concomitant tumor recurrence, in particular for controlling cancer stem cell stemness, clonogenicity, proliferation and/or survival, and/or tumor growth in a subject, wherein said polypeptide or polypeptide fragment induces an antibody response sufficient to neutralize or antagonize endogenous NANOG in said subject. In a preferred aspect of this embodiment, the subject is suffering from cancers and/or tumors selected from the group consisting of hematopoietic cancers, brain cancer, breast cancer, colorectal cancer, head and neck cancer, pancreatic cancer, lung cancer, liver cancer, melanoma, prostate cancer, muscle cancer and mesenchymal cancer, more preferably brain cancer and/or tumor.

In another embodiment of the invention a use is provided of a NANOG polypeptide or a NANOG polypeptide fragment, typically a synthetic polypeptide corresponding to epitopes of NANOG, for the preparation of a pharmaceutical composition for the prevention, repression or treatment of cancers and/or tumors linked to cancer stem cells in a subject, wherein said polypeptide or polypeptide fragment induces an antibody response sufficient to neutralize or antagonize endogenous NANOG in said subject. In a preferred aspect of this embodiment, the subject is suffering from cancers and/or tumors selected from the group consisting of hematopoietic cancers, brain cancer, breast cancer, colorectal cancer, head and neck cancer, pancreatic cancer, lung cancer, liver cancer, melanoma, prostate cancer, muscle cancer and mesenchymal cancer.

In a preferred aspect of this embodiment, a use is provided of a NANOG polypeptide or a NANOG polypeptide fragment for the preparation of a pharmaceutical composition for the prevention, repression or treatment of brain cancer and/or tumor, more preferably glioblastoma multiforme.

In another embodiment of the invention a method is provided for controlling cancer stem cell persistence and concomitant tumor recurrence, in particular for controlling cancer stem cell stemness, clonogenicity, proliferation and/or survival, and/or for controlling tumor growth in a subject, said method comprising administering to a subject in need thereof an amount of a NANOG polypeptide or a NANOG polypeptide fragment, or a pharmaceutical formulation thereof sufficient to induce an antibody response sufficient to neutralize or antagonize endogenous NANOG in said subject. In a preferred aspect of this embodiment, the subject is suffering from cancers and/or tumors selected from the group consisting of hematopoietic cancers, brain cancer, breast cancer, colorectal cancer, head and neck cancer, pancreatic cancer, lung cancer, liver cancer, melanoma, prostate cancer, muscle cancer and mesenchymal cancer, more preferably brain cancer and/or tumor.

In another embodiment of the invention a method is provided of preventing, repressing or treating cancers and/or tumors linked to cancer stem cells in a subject, said method comprising administering to a subject in need thereof an amount of a NANOG polypeptide or a NANOG polypeptide fragment, or a pharmaceutical formulation thereof sufficient to induce an antibody response sufficient to neutralize or antagonize endogenous NANOG in said subject. In a preferred aspect of this embodiment, the subject is suffering from cancers and/or tumors selected from the group consisting of hematopoietic cancers, brain cancer, breast cancer, colorectal cancer, head and neck cancer, pancreatic cancer, lung cancer, liver cancer, melanoma, prostate cancer, muscle cancer and mesenchymal cancer, more preferably brain cancer and/or tumor.

In a further embodiment of the invention a use or a method according to the invention is provided wherein the subject is displaying signs or symptoms of a condition involving cancers and/or tumors selected from the group consisting of hematopoietic cancers, brain cancer, breast cancer, colorectal cancer, head and neck cancer, pancreatic cancer, lung cancer, liver cancer, melanoma, prostate cancer, muscle cancer and mesenchymal cancer.

In another further embodiment of the invention a use or a method according to the invention is provided wherein the subject is suffering from brain cancer and/or tumor, preferably glioblastoma multiforme.

In a further embodiment of the invention a use or a method according to the invention is provided wherein the subject is predisposed to develop cancers and/or tumors, preferably cancers and/or tumors selected from the group consisting of hematopoietic cancers, brain cancer, breast cancer, colorectal cancer, head and neck cancer, pancreatic cancer, lung cancer, liver cancer, melanoma, prostate cancer, muscle cancer and mesenchymal cancer, more preferably brain cancer and/or tumor, for example based on familial history.

In another embodiment, a use or a method according to the invention is provided wherein the NANOG antagonist is a neutralizing anti-NANOG antibody.

In a still further embodiment, a use or a method according to the invention is provided wherein the NANOG antagonist is a neutralizing anti-NANOG antibody as mentioned above conjugated directly or indirectly to the transferrin-like peptide of amino acid sequence SEQ ID NO: 41.

Compounds and compositions according to the invention may be useful in the control of cancer stem cell persistence and concomitant tumor recurrence, in particular control of cancer stem cell clonogenicity and/or proliferation, and/or control of tumor growth in a subject. In a particular embodiment, compounds and compositions according to the invention may be useful in the prevention, repression or treatment of cancers and/or tumors linked to cancer stem cells. In another particular embodiment, compounds and compositions according to the invention may be useful in the prevention, repression or treatment of cancers and/or tumors selected from the group consisting of haematopoietic cancers, brain cancer, breast cancer, colorectal cancer, head and neck cancer, pancreatic cancer, lung cancer, liver cancer, melanoma, prostate cancer, muscle cancer and mesenchymal cancer, preferably brain cancer and/or tumor, more preferably glioblastoma multiforme.

References cited herein are hereby incorporated by reference in their entirety. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein, will become apparent to those skilled in the art from the foregoing description and accompanying drawings. Such modifications are intended to fall within the scope of the appended claims.

The invention having been described, the following examples are presented by way of illustration, and not limitation.

EXAMPLES

The following abbreviations refer respectively to the definitions below:

aa (amino acid), bp (base pair), cm (centimeter), h (hour), µl (microliter), µM (micromolar), mM (millimolar), mg (milligram), min (minute), nm (nanometer), BIT (bovine serum albumin, insulin and transferrin in Iscove's Modified Dulbecco's Medium), DAPI (4',6-diamidino-2-phenylindole), DMEM (Dulbecco's modified eagle medium), EDTA (ethylene diamine tetraacetic acid), EGF (Epidermal Growth Factor), FACS (Fluorescence-activated cell sorting), F12 (Nutrient Mixture F-12), FGF (Fibroblast Growth Factor), GFP (Green Fluorescent Protein), HEPES (N-2-hydroxyethylpiperazine-N'-2-ethanesulfonic acid), HBSS (Hank's Balanced Salt Solution), HINGS (Heat Inactivated Goat Serum), kd (knock down), LB (Luria Broth), PBS (Phosphate saline buffer), PCR (Polymerase Chain Reaction), PBT (PBS-0.1% Triton), PFA (paraformaldehyde), PTCH1 (Protein patched homolog 1), RPM (rotation per minute), RT (reverse transcriptase), SMOH (smoothened gene), RIPA (RadioImmunoPrecipitation Assay), shRNA (short hairpin RNA), TBP (TATA-binding protein), WT (wild-type).

Materials and Methods

Tumor dissociation, cell culture, FACS analyses

Fresh tumor samples or xenografts were manually dissociated after incubation in papain-containing 5.5 mM L-cystein, 1.1 mM EDTA at 37° C. for 1 h, followed by treatment with DNAse (Roche) and Ovomucoid (BD bioscience), filtered with a 70µm filter (Millipore), washed in PBS and cultured in gliomasphere media (2/3 DMEM F12, 20% BIT 9500 (stem cell technology), FGF 10ng/µl, EGF 10ng/µl and 1% pen/strep, plus 1/3 filtered conditioned media). Primary glioma adherent cells were cultured on Laminin as described (Pollard et al., 2009, *Cell Stem Cell*, 4, 568-580). U87MG and U251 were cultured as described (Stecca and Ruiz i Altaba, 2009, supra). For FACS analyses cells were manually dissociated, resuspended in PBS-EDTA 5 mM and analyzed for their red and green fluorescence using a FACS Calibur machine (BD bioscience). Primary tumors are described previously (Clement al., 2007, *Curr Biol.*, 17, 165-172). Additional tumors were: GBM-14: right rolandic plus corpus callosum, female, 83 years old; GBM-15: right fronto-parietal, male, 45; GBM-16: left temporo-occipital, male, 62; GBM-17: left frontal, female, 73. IDH1 and IDH2 sequencing of GBMs used primers described in Hartmann et al. (2009, *Acta Neuropathol.* 118, 469-74). p53 sequencing of exons 5-9 was as described (Stecca and Ruiz i Altaba, 2009, *Embo J.*, 28, 663-676). U87 were infected with lentivectors and 20,000 cells/well were plated 48h later in medium containing from increasing concentration of temozolomide. Cells were harvested and counted 5 days later. All tumors were obtained with patient consent locally in Geneva (Clement et al., 2007, supra) and under approved protocols at La Salpetrière Hospital, Paris, France. CD133 magnetic activated cell sorting (MACS) and fluorescent activated cell sorting (FACS) were as described in Varnat et al. (2009, *EMBO Mol. Med.* 1, 338-51).

RT-PCR and quantitative RT-PCR

Total RNA extracted with micro or miniRNA easy kits (Qiagen) or Trizol (Invitrogen) was treated with DNAseI and cDNA synthesized by random priming. Quantitative real time (q) PCR used iQTm SYBR green mix (BioRad). Reactions were at 60° C. using an Opticon PCR apparatus from MJ Research. The level of each target gene was normalized using the geometrical mean of TBP and BETA ACTIN. OCT4 (POU5F1) primers pick OCT4 plus 12/13 pseudogenes. Other PCRs were performed using Phusion polymerase (Finnzymes). RT-PCR primers were as described (Clement et al., 2007, supra; Varnat et al., 2009, supra) with the exception of the following written 5' to 3':

| | | |
|---|---|---|
| NANOG/P8-fw | AAATTGGTGATGAAGATGTATTCG | (SEQ ID NO: 14) |
| NANOG/P8-rev | GCAAAACAGAGCCAAAAACG | (SEQ ID NO: 15) |
| NANOPG8-fw | GCTGCCTTCAAGCATCTGTT | (SEQ ID NO: 16) |
| NANOGP8-rev | TTGTTTGCCTTTGGGACTGGT | (SEQ ID NO: 17) |
| NANOG/P8 3'UTR-fw | GGATGGTCTCGATCTCCTGA | (SEQ ID NO: 18) |

```
NANOG/P8    CCCAATCCCAAACAATACGA  (SEQ ID NO: 19)
3'UTR-rev

BETA        TGGAGAAAATCTGGCACCAC  (SEQ ID NO: 20)
ACTIN-      ACC
fw

BETA        GATGGGCACAGTGTGGGTGA  (SEQ ID NO: 21)
ACTIN-      CCC
rev

TBP-fw      TGCACAGGAGCCAAGAGTGAA (SEQ ID NO: 22)

TBP-rev     CACATCACAGCTCCCCACCA  (SEQ ID NO: 23)

PTCH1-fw    GGCAGCGGTAGTAGTGGTG   (SEQ ID NO: 24)
            TTC

PTCH1-rev   TGTAGCGGGTATTGTCGTG   (SEQ ID NO: 25)
            TGTG

SMOH-fw     GGGAGGCTACTTCCTCATCC  (SEQ ID NO: 26)

SMOH-rev    GGCAGCTGAAGGTAATGAGC  (SEQ ID NO: 27)

TP53-fw     GTGGAAGGAAATTTGCGTGT  (SEQ ID NO: 28)

TP53-rev    CCAGTGTGATGATGGTGAGG  (SEQ ID NO: 29)

SUFUH-fw    GGCTTTGAGTTGACCTTTCG  (SEQ ID NO: 30)

SUFUH-rev   CATCTGTGGGTCCTCTGTCA  (SEQ ID NO: 31)
```

Primers for 3'UTR sequencing were: 3'UTR-fw GAGACGGGGTTTCACTGTGT (SEQ ID NO: 32) and 3'UTR-rev CACTCGGTGAAATCAGGGTAA (SEQ ID NO: 33). PCR products were then cloned in pCRII-TOPO vector (Invitrogen) and ±20 individual clones were grown and sequenced.

Lentivectors 293T cells were transfected with calcium chloride using the VSV-G envelope plasmid pMD2G plasmid, packaging R8.74 plasmid, and the following lentivectors: parental pLL3.7, pLL3.7-shNANOG-1 (comprising SEQ ID NO: 11 GGGTTAAGCTGTAACATACTT; Zaehres et al., 2005, Stem Cells, 23, 299-305), pLKO-shNANOG-2 (comprising SEQ ID NO: 12 CCTGGAACAGTCCCTTCTATA; Biocat), pLL3.7-shNANOGP8 (comprising SEQ ID NO: 13 AACAAAGCACATCTTGCCAGGA); pliveen-NANOG; pRZ NANOG->Red (System Biosciences), pTW-GLI1, pTW-GLI3R, pLVCTH-shPTCH1 (Varnat et al., 2009, supra), pLVCTH-shSMOH (Clement et al., 2007, Curr Biol., 17, 165-172) and pLV-WPXL-shp53 (targeting human p53). A cDNA from the ATG to the stop codon of NANOG was synthesized from human fetal brain RNA and cloned in frame with a Flag tag in pFLAG-CMV2 (Sigma) vector. Flag-NANOG was then XbaI-XhoI cloned behind the CMV promoter in the pRRL-CMV-PGK-GFP-WPRE (pTWEEN) lentivector. Supernatants were harvested and concentrated by ultracentrifugation. Concentrated viruses were titrated and added to U87 cells, attached or dissociated gliomaspheres for 2 days to achieve >80% infection corresponding to MOI of ~2. Transduced cells were then washed and collected 2-3 days later for analysis.

Clonogenic assays

Transduced cells were dissociated and plated at 1 cell/well in 96-well plate in gliomasphere media, in triplicate, for each experiment. The number of total and of GFP$^+$ clones was determined using an inverted optical microscope with epifluorescence (Zeiss).

BrdU incorporation assays and immunodetection

BrdU pulses were performed for 16 hours for gliomaspheres and for 1 hour for U87 and U251 cells. Gliomaspheres were dissociated and plated on matrigel 1:1000 (BD Biosciences) for 30 min to allow attachment and fixed with ice-cold PFA (4%) for 30 seconds, followed by extensive washing with ice-cold PBS and PBT (PBS-0.1% Triton). Anti-NANOG (Kamiya rabbit#PC-102), anti-PML rabbit SC-5621 and mouse SC-996 (Santa Cruz), 54BP1(a kind gift of Thanos Halazonetis, U. Geneva), or anti-FLAG epitope (SIGMA M2 clone) antibodies were applied after blocking with PBT plus 10% heat inactivated goat serum (HINGS) overnight at 4° C. Secondary anti-rabbit Cy3 labelled were applied at 1/1000. For BrdU assays (anti-BrdU Ab used at 1/5000; University of Iowa Hybridoma Bank), cells were incubated first with 10% HCl for 15 min at room temperature and then blocked with borax 0.1M for 10 min at room temperature before blocking. Secondary anti-mouse rodamine labelled (Santa Cruz) (1:500) were diluted in PBT-10% HINGS for 45 min at room temperature. After washing, cells were stained with DAPI (Sigma) 1:10,000 for 2 min, mounted in PBS/glycerol with a pinch of PPDA and analysed under fluorescent Axiphot or confocal LSM-meta microscopes (Zeiss). For proliferation assays, 10 independent fields of BrdU/DAPI labelled cells were counted per condition.

Red/Green in vitro assays and orthotopic xenografts

For in vitro red/green assays (Varnat et al., 2009, supra), GBM-8 gliomaspheres or U87 cells were infected with LV-shNANOG-1 or LV-GFPcontrol-1 and mixed with sibling LV-RFP transduced cells at a ratio 1:1. After 5 days, magnetic CD133 sorting was performed (CD133 MicroBead Kit, Myltenyi Biotec), and the GFP/Red ratio was determined by FACS analysis on the different fractions. For in vivo red/green assays, $10^5$ dissociated cells were resuspended in 5 µl of HBSS and injected intracranially at coordinates {x,y,z=−2,−1,−2.5} relative to the bregma point using a stereotaxic apparatus. Fluorescence of xenografts was visualized in situ using dual red and green fluorescence excitation lasers in a special dark chamber with a color CCD camera (Lightools Research), and digitally recorded. Mice were sacrificed at the first signs of neurological disease.

Western blotting

Proteins were harvested in cold RIPA buffer 4 days after U87 cell transduction, incubated on ice for 20 min and centrifuged at 13000 RPM at 4° C. for 20 min. Supernatants were collected and measured for protein concentration (BCA protein Assay, Pierce). 20 µg of total protein for HSP90 and p53 and 80 µg for GLI1 were run on a SDS-page gel and transferred on a nitrocellulose membrane overnight at 4° C. Membranes were blocked in PBT-5% skimmed milk and blotted with anti-p53 (1/2000) (mouse, Santa Cruz, Clone DO-1) or HSP90 (1/4000) (mouse, Santa Cruz, Clone F-8) antibodies for 1 h at room temperature, or GLI1 affinity-purified polyclonal antibodies (Stecca and Ruiz i Altaba, 2009, supra) overnight at 4° C. Secondary antibodies (anti-mouse HRP (1/6000) (Promega) or anti-rabbit HRP (1/2000) (Promega) were incubated for 1 h at room temperature. Signal on membranes was revealed with ECL (Thermo Scientific) for HSP90 and p53 or with SuperSignal West Femto Maximum Sensitivity Substrate (Thermo Scientific) for GLI1.

Luciferase reporter assay

GLI-binding site luciferase reporter and lentiviral/plasmid constructs (e.g. Stecca and Ruiz i Altaba, 2009, supra; Varnat et al., 2009, supra) were transfected in U87 cells with Fugene (Roche). Renilla controls were included in all cases

Example 1

Expression of Nanog/Nanogp8 in Gbms

To test for the presence in GBMs of the two NANOG-encoding transcripts, we assayed for NANOG and NANOGP8 mRNAs (together referred as NANOG/P8) by quantitative RT-PCR, normalizing the values with those of TBP and βACTIN. NANOGP8 encodes NANOG protein with only 2 or 3 amino acid changes in comparison with each of the NANOG alleles. In addition to NANOG and NANOGP8 there are 10 non-coding NANOG pseudogenes. Their sequences are not recognized by the PCR primers used here.

All primary GBMs (gliomas WHO grade IV), lower grade astrocytomas and oligodendrogliomas (gliomas WHO grade III and II) tested expressed NANOG/P8 albeit to different levels (FIG. 1).

The results show that all brain tumors tested express NANOG and NANOGP8 mRNAs.

This provides evidence that all GBM cells express NANOG-encoding genes, and that NANOG is present and active in, but not restricted to, GBM stem cells.

Example 2

Nanog Function Modulates Gbm Clonogenicity and Proliferation In Vitro

To test for the function of NANOG we have used two independent shRNAs expressed from replication incompetent lentivectors: shNANOG-1 (SEQ ID NO: 11) which targets the 3'UTR in a GFP+ lentivector and shNANOG-2 (SEQ ID NO: 12) which targets exon 4, with 50-70% efficiencies for mRNA degradation and 80-90% for protein. Each of these shRNAs inhibits both NANOG and NANOGP8. This strategy ensures the targeting of all NANOG encoding genes. Indeed, Western blot analyses showed that Kamiya rabbit#PC-102 antibody identified the endogenous and exogenous 42kD NANOG protein in U87 cells and that NANOG knock-down (kd) led to a near complete loss of endogenous NANOG protein.

NANOG kd was first performed in gliomaspheres. Single-cell clonogenic assays over 2 weeks showed that NANOG kd reduced the number of GFP+ gliomaspheres by 20-80%, as compared with control parental lentivectors. NANOG is thus required for normal clonogenic behavior of GBM stem cells.

Gliomaspheres with NANOG kd were also ~2.5-fold smaller than controls. Consistently, BrdU incorporation analyses in plated gliomaspheres of 5 primary GBMs showed 20-40% reduction in cell proliferation, and 30-60% in the U87 and U251 GBM cell lines, after NANOG kd.

Therefore, NANOG is required both for normal proliferative levels of GBM stem cells, and for the clonogenicity of putative GBM stem cells.

Example 3

Role of Nanog in Tumorigenicity and Tumor Growth In Vivo

Figure 2:
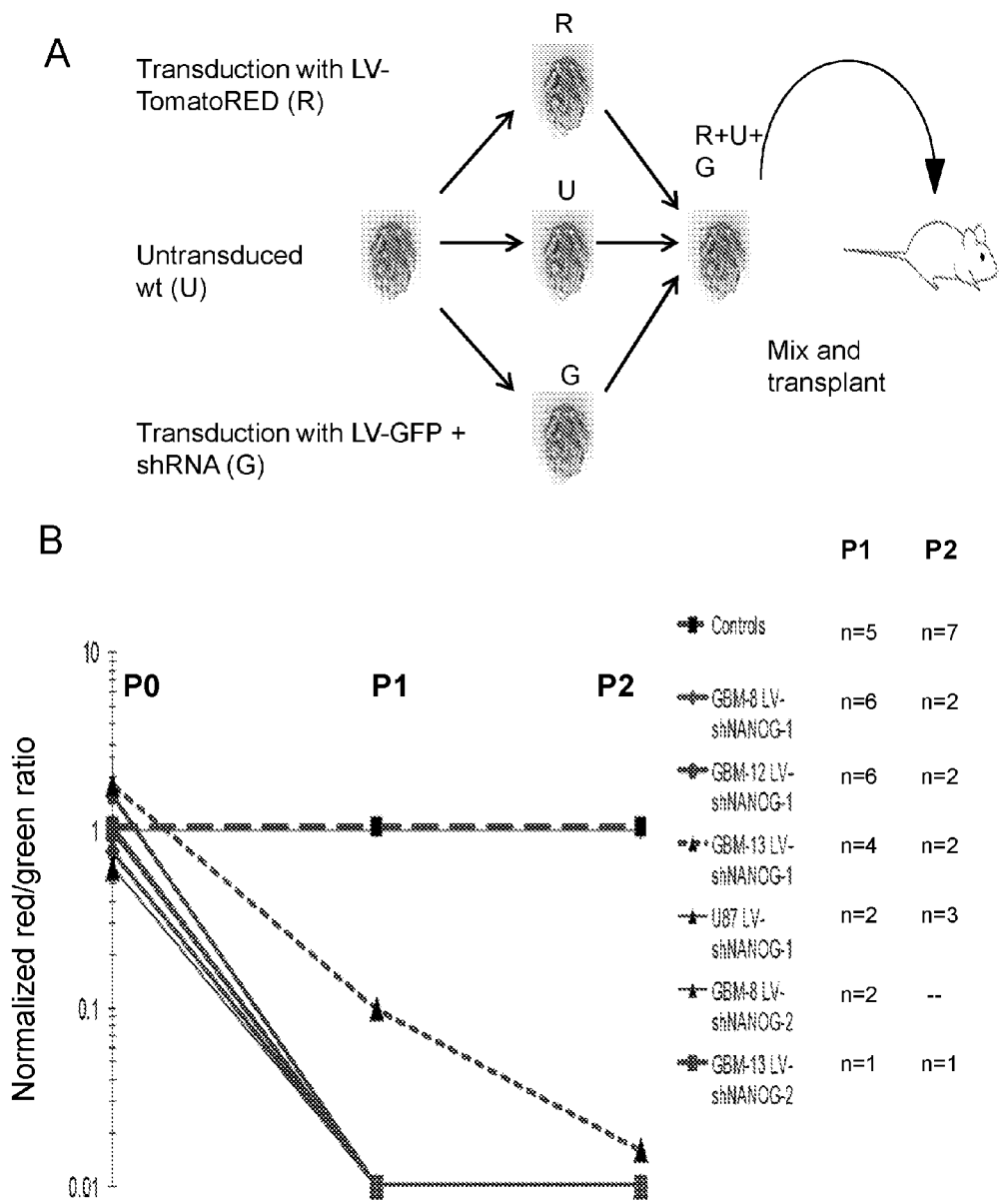
FIG. 2 shows (A) a scheme of the orthotopic red/green competition assay with GBM cells; (B) quantification of FACS ratios in red/green competition assays in vivo after normalization with controls, which are equated to 1, which shows that NANOG function is essential for tumor growth and survival. The number of mice analyzed at each passage (P) is also given (n) for each case. Primary tumor cells treated with shRNA to knock down NANOG exhibit poor survival when transplanted into recipient mice compared with similar cells in which NANOG function is unaffected.

To test for the role of NANOG in vivo, we used the novel in vivo red/green assay in which tumor cells that are differently and indelibly marked compete within a tumor environment. Cancer cells comprising equivalent populations of transduced cells expressing different fluorescent proteins (see above) are mixed in xenografts in immunocompromised mice, thus allowing for competition in vivo (FIG. 2A). The grown tumor is then isolated, cells dissociated, an aliquot is subjected to FACS quantification, and the rest re-injected into a new host, repeating the cycle as long as required. Here we have extended this assay to use it in orthotopic intracranial xenografts with primary GBM cells.

Injection of $10^5$ GBM cells comprising mixed populations as described above showed that three patient-derived GBMs (GBM-8, GBM-12 and GBM-13) and U87 cells showed a rapid and massive loss of GFP+ cells expressing NANOG shRNAs in vivo, within the first passage, as compared with sibling RFP+ cells in the same tumors (FIG. 2B). GFP-only controls showed limited variability and were used for normalization. Similar effects were obtained with a second shRNA confirming the specificity of the targeting (FIG. 2B). These results identify NANOG as an essential factor for GBM tumor growth.

In summary, NANOG function in human GBMs has been studied by blocking its function through RNAi targeting both NANOG and NANOGP8, as well NANOGP8 alone. The most striking results reveal that NANOG function is essential for GBM tumorigenicity in a cell autonomous manner in vivo in immunocompromised mice. Patient-derived GBM cells with NANOG and NANOGP8 kd or NANOGP8 kd alone do not survive and do not form tumors, indicating that NANOG function, mostly derived from NANOGP8, is essential for GBM tumorigenicity in vivo.

Example 4

Role of Nanog in HH-GLI Signalling

Figure 3:
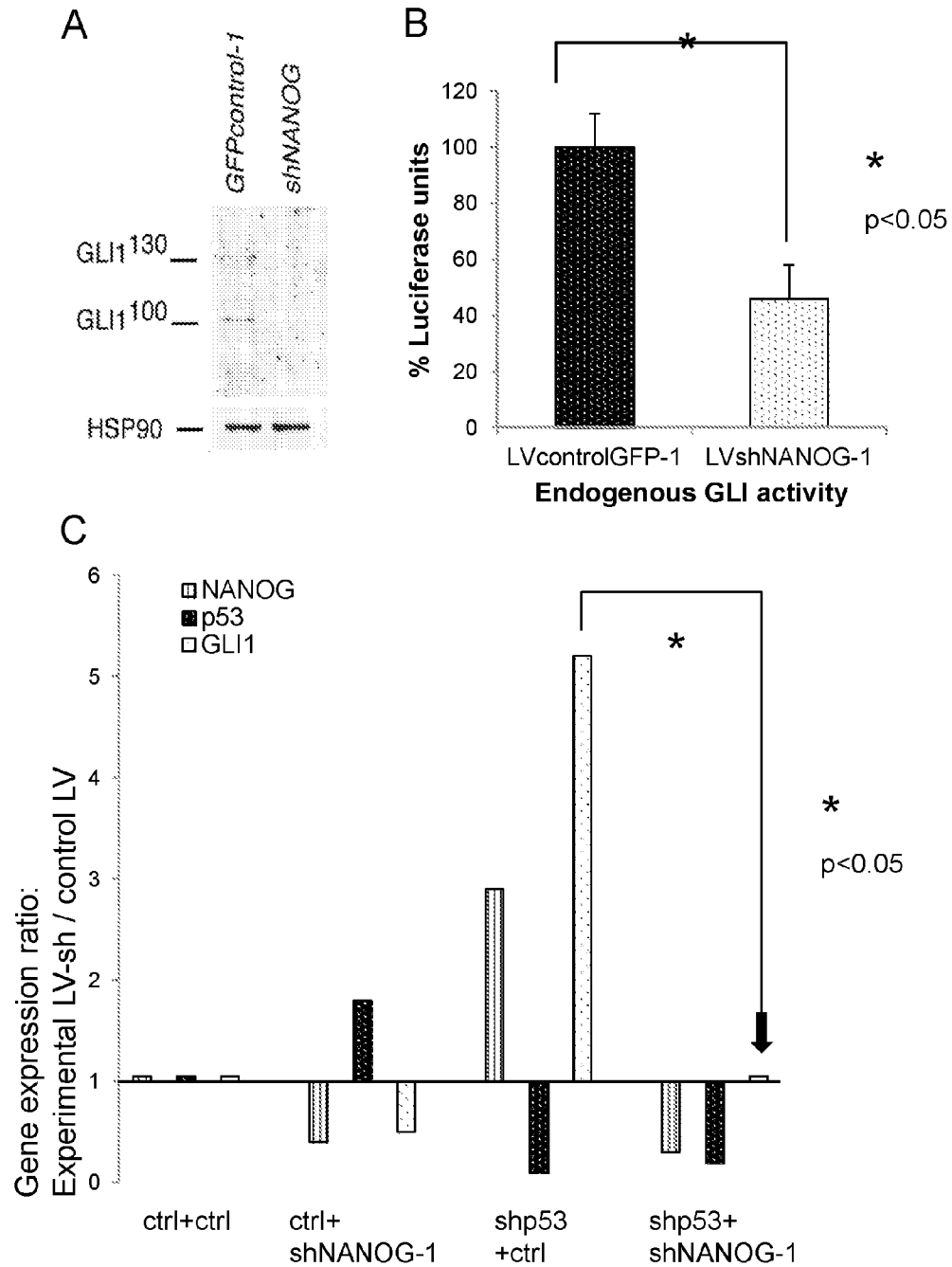
FIG. 3 shows the functional interactions of NANOG, GLI and P53 in GBM cells. (A) GLI protein isoforms are inhibited by knockdown of NANOG in U87 (GBM) cells. (B) GLI-binding site-Luciferase reporter assays testing for the activity of endogenous GLI1 in U87 cells. Endogenous GLI activity in U87 (GBM) cells is reduced by knockdown of NANOG. (C) GLI expression levels in U87 (GBM) cells are reduced by knockdown of NANOG only, but normalized by concomitant knockdown of NANOG and P53.

NANOG kd greatly decreased GLI protein levels by Western blot (of $GLI1^{100}$ or $GLI1^{130}$ isoforms; Stecca and Ruiz i Altaba, 2009, supra) (FIG. 3A). Consistently, the levels of activity of a GLI-binding site->Luciferase reporter were reduced after kd of NANOG (FIG. 3B). Together with our previous data on the modulation of NANOG/P8 mRNA levels by HH signaling in different systems (Stecca and Ruiz i Altaba, 2009, supra), these results suggest the presence of a positive loop between NANOG and GLI1.

An important repressor of NANOG in mouse ES cells is the tumor suppressor p53 (Lin et al., 2005, *Nat. Cell Biol*, 7, 165-171). P53 also establishes a functional negative regulatory loop with GLI1 in neural stem cells and tumors (Stecca and Ruiz i Altaba, 2009, supra).

To clarify the relationship of NANOG, GLI1 and p53, gene expression profiles were determined by RT-qPCR in U87 cells after kd of NANOG, kd of p53 or simultaneous kd of both. Expression levels were normalized with the levels in housekeeping genes and shown as ratios over those in control-transduced cells (FIG. 3C): NANOG kd enhanced p53 and repressed GLI1, whereas p53 kd greatly boosted both NANOG and GLI1. Importantly, simultaneous kd of both NANOG and p53 restored GLI1 to control levels (FIG. 3C, arrow). Control lentivectors had no effect. This result suggests that the decrease of GLI1 after NANOG kd requires p53, and that its enhancement after kd of p53 requires NANOG. The decrease in reporter activity by exogenous GLI1 after NANOG kd (see above) is thus likely mediated, in part, by enhanced endogenous p53 levels,

Example 5

Nanog and HH-GLI Signalling Specifically in Gbms

Figure 4:
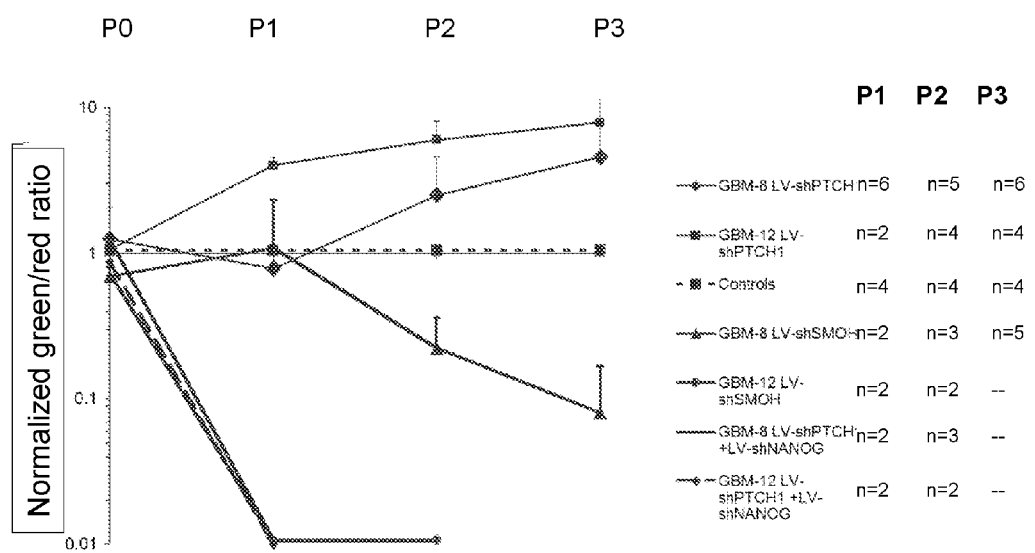
FIG. 4 represents the quantification and evolution of FACS ratios in red/green competition assays in vivo after normalization with controls, which are equated to 1. The number of mice analyzed at each passage (P) is also given (n) for each case. NANOG is a mediator of HH-GLI signaling in GBM cells. HH-GLI activity may be modified by knockdown of PTCH1 (enhances expression of GLI) or by knockdown of SMOH (represses expression of GLI). However, simultaneous knockdown of PTCH1 and NANOG obliterates the population of over-expressing cells to at least the level of SMOH knockdown.

To test if NANOG is a mediator of HH-GLI signaling in GBMs, acting downstream of GLI1, we performed in vivo epistatic analyses using orthotopic xenografts. Enhanced HH-GLI activity through shPTCH1 resulted in an increase in the population of $GFP^+$/shPTCH1 expressing cells in intracerebral red/green assays (FIG. 4). In contrast, shNANOG obliterated the expressing population. However, shNANOG was epistatic over shPTCH1 in GBM-8 and GBM-12, indicating that NANOG is essential for HH-GLI responses in GBMs in vivo.

The results show that NANOG and GLI1 form a positive loop in which the normal levels of expression of one are dependent on the function of the other. In addition, since analyses in vivo show that NANOG is essential for HH-GLI responses, we conclude that NANOG function is a key GLI1 effector. NANOG and GLI1 thus form a functionally relevant positive module, the levels of which regulate tumor growth.

Example 6

Construction of Nanog Dominant-Negative Polypeptides and Test Of In Vitro and In Vivo Activity Different nucleic acid constructs are prepared which encode NANOG dominant-negative polypeptides in relation to the action of NANOG as a transcriptional activator, comprising:
 (i) NANOG homeodomain (SEQ ID NO: 5);
 (ii) one repressor domain selected among that of an Engrailed protein (such as SEQ ID NO: 36 and SEQ ID NO: 38), that of Pit-1 beta (SEQ ID NO: 37), that of IRF1 (SEQ ID NO: 39), and the WRPW motif of the hairy-related protein (SEQ ID NO: 44), fused at the C-terminal part of the NANOG homeodomain;
 (iii) tags selected from FLAG (SEQ ID NO: 42) and HA (SEQ ID NO: 43), fused at the N-terminal part or C-terminal part of the chimeric polypeptide.

The NANOG dominant-negative polypeptides are expressed in cells from recombinant doxycycline-inducible conditional lentivectors (STEMCCA) and their effect to reduce proliferation and clonogenicity tested in U87-MG GBM cells in vitro.

For in vivo tests, purified NANOG dominant-negative polypeptides are administered by infusion into the brains of mice through the use of cannulas and Alzet osmotic minipumps.

Regimens of 3-14 days with different protein concentrations are first used to monitor the chimeric polypeptide localization and levels in the normal brain. Similar experiments are performed with cohorts of mice harboring intracranially implanted ($5 \times 10^3$-$10^5$) $GFP^+$ human GBM cells, 3-6 weeks after cell implantation when the tumor should already be growing (mice usually succumb after about 2-3 months). The levels and presence of the chimeric polypeptides are determined using anti-FLAG or anti-HA tag antibodies in $GFP^+$ human GBM cells. Tumor volume, BrdU incorporation, cleaved Caspase3+ apoptosis, invasion and time before disease detection are also measured. Carrier only and scrambled peptide pumps are used as controls.

Example 7

Construction of a Nanog Dominant-Negative Polypeptide Useful for Systemic Therapy A nucleic acid construct is prepared which encodes a NANOG dominant-negative polypeptide comprising:
 (i) antennapedia peptide penetratin (SEQ ID NO: 40);
 (ii) glioma targeting peptide of SEQ ID NO: 41;
 (iii) NANOG homeodomain (SEQ ID NO: 5); and
 (iv) Pit-1beta repressor domain (SEQ ID NO: 37).

A disulfide bonds links the antennapedia penetratin and glioma targeting peptide.

Tags selected from FLAG and HA are fused at the N-terminal part or C-terminal part of the chimeric polypeptide.

The resulting encoded fusion protein constitutes a NANOG dominant-negative polypeptide that can be administered systemically for cancer therapy.

---

SEQUENCE LISTING

SEQ ID NO. 1: amino acid sequence of Human NANOG Isoform 1
(UNIPROT accession Q9H9S0-1)
MSVDPACPQSLPCFEASDCKESSPMPVICGPEENYPSLQMSSAEMPHTETVSPLPSSM
DLLIQDSPDSSTSPKGKQPTSAEKSVAKKEDKVPVKKQKTRTVFSSTQLCVLNDRFQ
RQKYLSLQQMQELSNILNLSYKQVKTWFQNQRMKSKRWQKNNWPKNSNGVTQKA
SAPTYPSLYSSYHQGCLVNPTGNLPMWSNQTWNNSTWSNQTQNIQSWSNHSWNTQ
TWCTQSWNNQAWNSPFYNCGEESLQSCMQFQPNSPASDLEAALEAAGEGLNVIQQT
TRYFSTPQTMDLFLNYSMNMQPEDV SEQ ID NO. 2: amino acid sequence of a natural variant of
Human NANOG Isoform 1
MSVDPACPQSLPCFEASDCKESSPMPVICGPEENYPSLQMSSAEMPHTETVSPLPSSM
DLLIQDSPDSSTSPKGKQPTSAENSVAKKEDKVPVKKQKTRTVFSSTQLCVLNDRFQ
RQKYLSLQQMQELSNILNLSYKQVKTWFQNQRMKSKRWQKNNWPKNSNGVTQKA
SAPTYPSLYSSYHQGCLVNPTGNLPMWSNQTWNNSTWSNQTQNIQSWSNHSWNTQ
TWCTQSWNNQAWNSPFYNCGEESLQSCMQFQPNSPASDLEAALEAAGEGLNVIQQT
TRYFSTPQTMDLFLNYSMNMQPEDV SEQ ID NO. 3: amino acid sequence of Human NANOG Isoform 2
(UNIPROT accession Q9H9S0-2)
MSVDPACPQSLPCFEASDCKESSPMPVICGPEENYPSLQMSSAEMPHTETVSPLPSSM
DLLIQDSPDSSTSPKGKQPTSAEKSVAKKEDKVPVKKQKTRTVFSSTQLCVLNDRFQ

| SEQUENCE LISTING |
| --- |

RQKYLSLQQMQELSNILNLSYKQVKTWFQNQRMKSKRWQKNNWPKNSNGVTQGC
LVNPTGNLPMWSNQTWNNSTWSNQTQNIQSWSNHSWNTQTWCTQSWNNQAWNS
PFYNCGEESLQSCMQFQPNSPASDLEAALEAAGEGLNVIQQTTRYFSTPQTMDLFLN
YSMNMQPEDV

SEQ ID NO. 4: amino acid sequence of Human NANOGP8 (Uniprot
accession Q6NSW7)
MSVDPACPQSLPCFEASDCKESSPMPVICGPEENYPSLQMSSAEMPHTETVSPLPSSM
DLLIQDSPDSSTSPKGKQPTSAENSVAKKEDKVPVKKQKTRTVFSSTQLCVLNDRFQ
RQKYLSLQQMQELSNILNLSYKQVKTWFQNQRMKSKRWQKNNWPKNSNGVTQKA
SAPTYPSLYSSYHQGCLVNPTGNLPMWSNQTWNNSTWSNQTQNIQSWSNHSWNTQ
TWCTQSWNNQAWNSPFYNCGEESLQSCMHFQPNSPASDLEAALEAAGEGLNVIQQT
TRYFSTPQTMDLFLNYSMNMQPEDV SEQ ID NO. 5: amino acid sequence of Human NANOG Homeodomain
KQKTRTVFSSTQLCVLNDRFQRQKYLSLQQMQELSNILNLSYKQVKTWFQNQRMKS
KRWQ SEQ ID NO. 6: amino acid sequence of Mouse (*Mus musculus*)
NANOG (Uniprot accession Q80Z64)
MSVGLPGPHSLPSSEEASNSGNASSMPAVFHPENYSCLQGSATEMLCTEAASPRPSSE
DLPLQGSPDSSTSPKQKLSSPEADKGPEEEENKVLARKQKMRTVFSQAQLCALKDRF
QKQKYLSLQQMQELSSILNLSYKQVKTWFQNQRMKCKRWQKNQWLKTSNGLIQK
GSAPVEYPSIHCSYPQGYLVNASGSLSMWGSQTWTNPTWSSQTWTNPTWNNQTWT
NPTWSSQAWTAQSWNGQPWNAAPLHNFGEDFLQPYVQLQQNFSASDLEVNLEATR
ESHAHFSTPQALELFLNYSVTPPGEI SEQ ID NO. 7: amino acid sequence of Bovine (*Bos
Taurus*) NANOG(Uniprot accession Q4JM65)
MSVGPACPQSLLGPEASNSRESSPMPEESYVSLQTSSADTLDTDTVSPLPSSMDLLIQD
SPDSSTSPRVKPLSPSVEESTEKEETVPVKKQKIRTVFSQTQLCVLNDRFQRQKYLSLQ
QMQELSNILNLSYKQVKTWFQNQRMKCKKWQKNNWPRNSNGMPQGPAMAEYPGF
YSYHQGCLVNSPGNLPMWGNQTWNNPTWSNQSWNSQSWSNHSWNSQAWCPQAW
NNQPWNNQFNNYMEEFLQPGIQLQQNSPVCDLEATLGTAGENYNVIQQTVKYFNSQ
QQITDLFPNYPLNIQPEDL SEQ ID NO. 8: amino acid sequence of Rat (*Rattus norvegicus*)
NANOG (Uniprot accession A8QWW8)
MSVDLSGPHSLPSCEEASNSGDSSPMPAVHLPEENYSCLQVSATEMLCTETASPPPSS
GDLPLQDSPDSSSNPKLKLSGPRLTRALRRKKRTRSSPRKQKMRTVFSQAQLCALKD
RFQRQRYLSLQQMQDLSTILSLSYKQVKTWFQNQRMKCKRWQKNQWLKTSNGLTQ
GSAPVEYPSIHCSYSQGYLMNASGNLPVWGSQTWTNPTWNNQTWTNPTWSNQTWT
NPTWSNQAWSTQSWCTQACNSQTWNAAPLHNFGEDSLQPYVPLQQNFSASDLEAN
LEATRESQAHFSTPQALELFLNYSVNSPGEI SEQ ID NO. 9: nucleotide sequence encoding human NANOG
isoform 1
ATGAGTGTGGATCCAGCTTGTCCCCAAAGCTTGCCTTGCTTTGAAGCATCCGACT
GTAAAGAATCTTCACCTATGCCTGTGATTTGTGGGCCTGAAGAAAACTATCCATC
CTTGCAAATGTCTTCTGCTGAGATGCCTCACACGGAGACTGTCTCTCCTCTTCCTT
CCTCCATGGATCTGCTTATTCAGGACAGCCCTGATTCTTCCACCAGTCCCAAAGG
CAAACAACCCACTTCTGCAGAGAAGAGTGTCGCAAAAAAGGAAGACAAGGTCCC
GGTCAAGAAACAGAAGACCAGAACTGTGTTCTCTTCCACCCAGCTGTGTGTACTC
AATGATAGATTTCAGAGACAGAAATACCTCAGCCTCCAGCAGATGCAAGAACTC
TCCAACATCCTGAACCTCAGCTACAAACAGGTGAAGACCTGGTTCCAGAACCAG
AGAATGAAATCTAAGAGGTGGCAGAAAACAACTGGCCGAAGAATAGCAATGG
TGTGACGCAGAAGGCCTCAGCACCTACCTACCCCAGCCTTTACTCTTCCTACCAC
CAGGGATGCCTGGTGAACCCGACTGGGAACCTTCCAATGTGGAGCAACCAGACC
TGGAACAATTCAACCTGGAGCAACCAGACCCAGAACATCCAGTCCTGGAGCAAC
CACTCCTGGAACACTCAGACCTGGTGCACCCAATCCTGGAACAATCAGGCCTGG
AACAGTCCCTTCTATAACTGTGGAGAGGAATCTCTGCAGTCCTGCATGCAGTTCC
AGCCAAATTCTCCTGCCAGTGACTTGGAGGCTGCCTTGGAAGCTGCTGGGGAAG
GCCTTAATGTAATACAGCAGACCACTAGGTATTTTAGTACTCCACAAACCATGGA
TTTATTCCTAAACTACTCCATGAACATGCAACCTGAAGACGTGTGA SEQ ID NO. 10: nucleotide sequence encoding human NANOGP8
ATGAGTGTGGATCCAGCTTGTCCCCAAAGCTTGCCTTGCTTTGAAGaATCCGACTG
TAAAGAATCTTCACCTATGCCTGTGATTTGTGGGCCTGAAGAAAACTATCCATCC
TTGCAAATGTCTTCTGCTGAGATGCCTCACACaGAGACTGTCTCTCCTCTTCCTTC
CTCCATGGATCTGCTTATTCAGGACAGCCCTGATTCTTCCACCAGTCCCAAAGGC
AAACAACCCACTTCTGCAGAGAAtAGTGTCGCAAAAAAGGAAGACAAGGTCCCG
GTCAAGAAACAGAAGACCAGAACTGTGTTCTCTTCCACCCAGCTGTGTGTACTCA
ATGATAGATTTCAGAGACAGAAATACCTCAGCCTCCAGCAGATGCAAGAACTCT
CCAACATCCTGAACCTCAGCTACAAACAGGTGAAGACCTGGTTCCAGAACCAGA
GAATGAAATCTAAGAGGTGGCAGAAAACAACTGGCCGAAGAATAGCAATGGT
GTGACGCAGAAGGCCTCAGCACCTACCTACCCCAGCCTcTACTCTTCCTACCAC
AGGGATGCCTGGTGAACCCGACTGGGAACCTTCCAATGTGGAGCAACCAGACCT

```
GGAACAATTCAACCTGGAGCAACCAGACCCAGAACATCCAGTCCTGGAGCAACC
ACTCCTGGAACACTCAGACCTGGTGCACCCAATCCTGGAACAATCAGGCCTGGA
ACAGTCCCTTCTATAACTGTGGAGAGGAATCTCTGCAGTCCTGCATGCAcTTCCA
GCCAAATTCTCCTGCCAGTGACTTGGAGGCTGCCTTGGAAGCTGCTGGGGAAGGC
CTTAATGTAATACAGCAGACCACTAGGTATTTTAGTACTCCACAAACCATGGATT
TATTCCTAAACTACTCCATGAACATGCAACCTGAAGACGTGTGA
```

SEQ ID NO. 11: nucleotide sequence of shNANOG1
GGGTTAAGCTGTAACATACTT

SEQ ID NO: 12: nucleotide sequence of shNANOG2
CCTGGAACAGTCCCTTCTATA

SEQ ID NO: 13: nucleotide sequence of shNANOGP8
AACAAAGCACATCTTGCCAGGA

SEQ ID NO: 14: NANOG/P8-fw primer
AAATTGGTGATGAAGATGTATTCG

SEQ ID NO: 15: NANOG/P8-rev primer
GCAAAACAGAGCCAAAAACG

SEQ ID NO: 16: NANOGP8-fw primer
GCTGCCTTCAAGCATCTGTT

SEQ ID NO: 17: NANOGP8-rev primer
TTGTTTGCCTTTGGGACTGGT

SEQ ID NO: 18: NANOG/P8 3'UTR-fw primer
GGATGGTCTCGATCTCCTGA

SEQ ID NO: 19: NANOG/P8 3'UTR-rev primer
CCCAATCCCAAACAATACGA

SEQ ID NO: 20: BETA ACTIN - fw primer
TGGAGAAAATCTGGCACCACACC

SEQ ID NO: 21: BETA ACTIN-rev primer
GATGGGCACAGTGTGGGTGACCC

SEQ ID NO: 22: TBP-fw primer
TGCACAGGAGCCAAGAGTGAA

SEQ ID NO: 23: TBP-rev primer
CACATCACAGCTCCCCACCA

SEQ ID NO: 24: PTCH1-fw primer
GGCAGCGGTAGTAGTGGTGTTC

SEQ ID NO: 25: PTCH1-rev primer
TGTAGCGGGTATTGTCGTGTGTG

SEQ ID NO: 26: SMOH-fw primer
GGGAGGCTACTTCCTCATCC

SEQ ID NO: 27: SMOH-rev primer
GGCAGCTGAAGGTAATGAGC

SEQ ID NO: 28: TP53-fw primer
GTGGAAGGAAATTTGCGTGT

SEQ ID NO: 29: TP53-rev primer
CCAGTGTGATGATGGTGAGG

SEQ ID NO: 30: SUFUH-fw primer
GGCTTTGAGTTGACCTTTCG

SEQ ID NO: 31: SUFUH-rev primer
CATCTGTGGGTCCTCTGTCA

SEQ ID NO: 32: 3'UTR-fw primer
GAGACGGGGTTTCACTGTGT

SEQ ID NO: 33: 3'UTR-rev primer
CACTCGGTGAAATCAGGGTAA

SEQUENCE LISTING

SEQ ID NO: 34: DNA binding consensus sequence of homeodomain proteins
[CG][GA][CG]C[GC]ATTAN[GC]

= srsCsATTAns (where s is c or g, and r is a or g, and n is c, g, t or a)

SEQ ID NO: 35: amino acid sequence of the W rich region of human NANOG involved in nuclear export and dimerization
WSNQTWNNSTWSNQTQNIQSWSNHSWNTQTWCTQSWNNQAWNSPF SEQ ID NO: 36: amino acid sequence of repressor domain of human Engrailed protein
MEEQQPEPKSQRDSALGGAAAATPGGLSLSLSPGASGSSGSGSDGDSVPVSPQPAPPS
PPAAPCLPPLAHHPHLPPHPPPPPQHLAAPAHQPQPAAQLHRTTNFFIDNILRPDFGC
KKEQPPPQLLVAAAARGGAGGGGRVERDRGQTAAGRDPVHPLGTRAPGAASLLCA
PDANCGPPDGSQPAAAGAGASKAGNPAAAAAAAAAVAAAAAAAAAKPSDTGGG
GSGGGAGSPGAQGTKYPEHGNPAILLMGSANGGPVVKTDSQQPLVWPAWVYCTRY
SDRPSSGPRTRKLKKKK SEQ ID NO: 37: Amino acid sequence of repressor domain of pituitary-specific positive transcription factor Pit-1beta
VPSILSLIQTPKCLHTYFSMTTMGNT SEQ ID NO: 38: amino acid sequence of repressor domain of the Drosophila Engrailed protein
MALEDRCSPQSAPSPITLQMQHLHHQQQQQQQQQQMQHLHQLQQLQQLHQQQLA
AGVFHHPAMAFDAAAAAAAAAAAAAHAHAAALQQRLSGSGSPASCSTPASSTPL
TIKEEESDSVIGDMSFHNQTHTTNEEEEAEEDDDIDVDVDDTSAGGRLPPPAHQQQST
AKPSLAFSISNILSDRFGDVQKPGKSMENQASIFRPFEASRSQTATPSAFTRVDLLEFSR
QQQAAAAAATAAMMLERANFLNCFNPAAYPRIHEEIVQSRLRRSAANAVIPPPMSSK
MSDANPEKSAL SEQ ID NO: 39: amino acid sequence of repressor domain of interferon regulatory factor-1 (IRF1)
MDATWLDSLLTPVRLPSIQAIPCAP SEQ ID NO: 40: amino acid sequence of penetratin from Antennapedia (Drosophila melanogaster)
RQIKIWFQNRRMKWKK SEQ ID NO: 41: amino acid sequence of a glioma targeting peptide
CRTIGPSVC SEQ ID NO: 42: amino acid sequence of the FLAG Tag
DYKDDDDK SEQ ID NO: 43: amino acid sequence of the HA (Human influenza hemagglutinin) Tag
YPYDVPDYA SEQ ID NO: 44: amino acid sequence of the WRPW motif of the hairy-related protein
WRPW

---

The invention claimed is:

1. A NANOG antagonist that is a NANOG dominant-negative polypeptide comprising a NANOG homeodomain fused to the repressor domain of a heterologous protein.

2. The NANOG antagonist according to claim 1, wherein the NANOG homeodomain has the amino acid sequence of SEQ ID NO:5, or the NANOG homeodomain is a NANOG homeodomain of a mammalian NANOG protein that binds to the DNA consensus sequence of SEQ ID NO:34.

3. The NANOG antagonist according to claim 1, wherein the repressor domain comprises the repressor domain of Pit-1beta (SEQ ID NO: 37), or the repressor domain of an Engrailed protein selected from SEQ ID NO: 36 or 38, the repressor domain of IRF1 (SEQ ID NO: 39), or the WRPW motif of the hairy-related protein (SEQ ID NO: 44).

4. The NANOG antagonist according to claim 1, wherein the NANOG dominant-negative polypeptide further comprises a cell penetrating peptide for translocating the polypeptide across the cell membrane and/or a brain tumor targeting peptide and/or a tag selected from SEQ ID NO: 42 or SEQ ID NO: 43 at the N-terminus or the C-terminus of the NANOG antagonist polypeptide.

5. The NANOG antagonist according to claim 4, wherein the cell penetrating peptide comprises penetratin from Antennapedia of SEQ ID NO: 40 and the brain tumor targeting peptide comprises a transferrin-like peptide of SEQ ID NO: 41.

6. The NANOG antagonist according to claim 1, wherein the NANOG dominant-negative polypeptide further comprises the dimerization domain of SEQ ID NO: 35.

7. A pharmaceutical formulation comprising a NANOG antagonist according to claim 1 and at least one pharmaceutically acceptable carrier.

8. The pharmaceutical formulation according to claim 7 further comprising a co-agent selected from bevacizumab, temazolomide, procarbazine, carmustine, or cilengitide.

9. A method of repressing or treating cancers linked to cancer stem cells in a subject, said method comprising administering to a subject in need thereof a therapeutically effective amount of a NANOG antagonist selected from:
   a) a NANOG dominant-negative polypeptide comprising a NANOG homeodomain fused to the repressor domain of a heterologous protein;
   b) a vector driving the expression of said NANOG antagonist; or
   c) a pharmaceutical formulation comprising a) or b).

10. The method of claim 9 wherein said cancers are brain cancers.

11. The method according to claim 9, wherein the NANOG homeodomain has the amino acid sequence of SEQ ID NO:5, or the NANOG homeodomain is a NANOG homeodomain of a mammalian NANOG protein that binds to the DNA consensus sequence of SEQ ID NO:34.

12. The method of claim 9, wherein the NANOG dominant-negative polypeptide further comprises a cell penetrating peptide for translocating the polypeptide across the cell membrane and/or a brain tumor targeting peptide and/or a Tag selected from FLAG of SEQ ID NO:42 and HA of SEQ ID NO:43 at the N-terminus or the C-terminus part of the NANOG antagonist.

13. The method according to claim 9, wherein the NANOG dominant-negative polypeptide is administered systemically.

14. A method of controlling cancer stem cell persistence and concomitant tumor recurrence in a subject comprising administering to a subject in need thereof an amount of a NANOG antagonist selected from:
   a) a NANOG dominant-negative polypeptide comprising a NANOG homeodomain fused to the repressor domain of a heterologous protein;
   b) a vector driving the expression of said NANOG antagonist; or
   c) a pharmaceutical formulation comprising a) or b).

15. A method of repressing or treating cancers linked to cancer stem cells in a subject, said method comprising administering to a subject in need thereof a therapeutically effective amount of a NANOG antagonist, wherein said NANOG antagonist is
   a) a short hairpin RNA selected from:
      i) shNANOG1 of nucleotide sequence SEQ ID NO:11,
      ii) shNANOG2 of nucleotide sequence SEQ ID NO:12 or
      iii) shNANOGP8 consisting of SEQ ID NO:13;
   b) a vector driving the expression of said NANOG antagonist; or
   c) a pharmaceutical formulation comprising a) or b).

16. The method of claim 15 wherein said cancers are brain cancers.

17. A method of controlling cancer stem cell persistence and concomitant tumor recurrence in a subject comprising administering to a subject in need thereof an amount of a NANOG antagonist, wherein said NANOG antagonist is
   a) a short hairpin RNA selected from:
      i) shNANOG1 of nucleotide sequence SEQ ID NO:11,
      ii) shNANOG2 of nucleotide sequence SEQ ID NO:12 or
      iii) shNANOGP8 consisting of SEQ ID NO:13;
   b) a vector driving the expression of said NANOG antagonist; or
   c) a pharmaceutical formulation comprising a) or b).

* * * * *